(12) United States Patent
Ling

(10) Patent No.: US 10,537,548 B2
(45) Date of Patent: Jan. 21, 2020

(54) COMPOSITION AND MEDICAL PRODUCT FOR REDUCING BODY WEIGHT AND BODY FAT, AND USE OF SAID PRODUCT

(71) Applicant: Caliway Biopharmaceuticals Co., Ltd., New Taipei (TW)

(72) Inventor: Yu-Fang Ling, New Taipei (TW)

(73) Assignee: CALIWAY BIOPHARMACEUTICALS CO., LTD., New Taipei (TW)

( * ) Notice: Subject to any disclaimer, the term of this patent is extended or adjusted under 35 U.S.C. 154(b) by 29 days.

(21) Appl. No.: 15/936,695

(22) Filed: Mar. 27, 2018

(65) Prior Publication Data

US 2018/0333388 A1 Nov. 22, 2018

Related U.S. Application Data

(63) Continuation-in-part of application No. 15/025,898, filed as application No. PCT/CN2015/088338 on Aug. 28, 2015.
(Continued)

(51) Int. Cl.
*A61K 8/06* (2006.01)
*A61K 31/353* (2006.01)
(Continued)

(52) U.S. Cl.
CPC ............ *A61K 31/353* (2013.01); *A23F 3/16* (2013.01); *A23L 33/105* (2016.08); *A61K 31/12* (2013.01);
(Continued)

(58) Field of Classification Search
CPC ....................................................... A61K 8/06
See application file for complete search history.

(56) References Cited

U.S. PATENT DOCUMENTS 6,475,530 B1 11/2002 Kuhrts
2003/0185912 A1 10/2003 Rosenbloom
(Continued)

FOREIGN PATENT DOCUMENTS

CN 101095665 1/2008
CN 101632655 1/2010
(Continued)

OTHER PUBLICATIONS

Meydani et al., "Dietary polyphenols and obesity", Nutrients, Jul. 2010; 2: 737-751.
(Continued)

*Primary Examiner* — Rosanne Kosson
(74) *Attorney, Agent, or Firm* — WPAT, PC

(57) ABSTRACT

The present invention discloses a composition and its pharmaceutical composition for reducing body weight and body fat, and a use of said product The composition comprises epigallocatechin gallate, curcumin, and an excipient, wherein the excipient comprises at least one of glyceryl dibehenate, polyoxyethylene stearates, polysorbate 80 mixture, vitamin E polyethylene glycol succinate, glyceryl monostearate, and oleoyl polyoxyl-6 glycerides, or a combination thereof; the polysorbate 80 mixture comprises polysorbate 80 and magnesium aluminometasilicate. In animal testing where obesity is induced either prior to or during testing, use of the composition of the present invention leads to a significant reduction of body weight and body fat.

33 Claims, 15 Drawing Sheets

Related U.S. Application Data

(60) Provisional application No. 62/477,514, filed on Mar. 28, 2017, provisional application No. 62/042,955, filed on Aug. 28, 2014.

(51) Int. Cl.
| | |
|---|---|
| A23F 3/16 | (2006.01) |
| A61K 45/06 | (2006.01) |
| A61K 36/82 | (2006.01) |
| A61K 31/12 | (2006.01) |
| A61K 31/4184 | (2006.01) |
| A61K 36/9066 | (2006.01) |
| A23L 33/105 | (2016.01) |

(52) U.S. Cl.
CPC .......... *A61K 31/4184* (2013.01); *A61K 36/82* (2013.01); *A61K 36/9066* (2013.01); *A61K 45/06* (2013.01); *A23V 2002/00* (2013.01); *A61K 2300/00* (2013.01)

(56) References Cited

U.S. PATENT DOCUMENTS

| | | |
|---|---|---|
| 2005/0147697 A1 | 7/2005 | Rosenbloom |
| 2006/0172012 A1 | 8/2006 | Finley et al. |
| 2008/0233218 A1 | 9/2008 | Newmark et al. |
| 2009/0239943 A1 | 9/2009 | Sarkar |
| 2012/0177623 A1 | 7/2012 | Naghavi et al. |
| 2014/0141082 A1 | 5/2014 | Gao |
| 2014/0271530 A1* | 9/2014 | Tummala ......... A61K 47/48176 424/78.31 |

FOREIGN PATENT DOCUMENTS

| | | |
|---|---|---|
| CN | 101695324 | 4/2010 |
| CN | 102357226 | 2/2012 |
| CN | 103479972 | 1/2014 |
| CN | 103717224 A | 4/2014 |
| CN | 103784421 A | 5/2014 |
| JP | 2012044982 A | 3/2012 |
| TW | 201707686 A | 3/2017 |
| TW | 201707722 A | 3/2017 |
| WO | WO2007041276 A2 | 4/2007 |
| WO | WO2008120220 A1 | 10/2008 |
| WO | WO2010048114 A1 | 4/2010 |
| WO | WO2013016257 A1 | 1/2013 |
| WO | WO2014028607 | 2/2014 |
| WO | WO2014111811 A1 | 7/2014 |
| WO | WO2017037594 A2 | 3/2017 |
| WO | WO2017049157 A1 | 3/2017 |

OTHER PUBLICATIONS

Most et al., "Short-term supplementation with a specific combination of dietary polyphenols increases energy expenditure and alters substrate metabolism in overweight subjects", Int J Obesity, May 2014; 38(5):698-706.

Shu Wang et al., "Novel insights of dietary polyphenols and obesity", Nutritional Biochemistry, Jan. 2014, vol. 25, pp. 1-18., 2013 Elsevier Inc.

Thérèse Sergent et al., "Phenolic compounds and plant extracts as potential natural anti-obesity substances", Accepted Apr. 14, 2012, Available online Apr. 21, 2012, pp. 68-73, T. Sergent et al. / Food Chemistry 135, , Elsevier Ltd.

Dong-Hu Zho et al., "Combination of Low Concentration of (—)-Epigallocatechin Gallate (EGCG) and Curcumin Strongly Suppresses the Growth of Non-Small Cell Lung Cancer in Vitro and in Vivo through Causing Cell Cycle Arrest", Accepted: May 28, 2013, Published: Jun. 5, 2013, pp. 12023-12036, International Journal of Molecular Sciences.

Mustika Ratu, "Slimming tea", Aug. 2009, Shopper.

New Chapter, "Whole Body Health Inflammation Response Dietary Supplement", Jun. 2014, Whole Foods Market.

* cited by examiner

A : Control
B : 1% polyoxyethylene (32) stearate
C : 0.5% polyoxyethylene (40) stearate
D : 5% polysorbate 80 mixture
E : 3% vitamin E polyethylene glycol succinate
F : 5% polysorbate 20
G : 1% PEG 400
H : 1% PEG 6000
I : 1% glyceryl monostearate
J : 1% oleoyl polyoxyl-6 glycerides
K : 1% glyceryl dibehenate

COMPOSITION AND MEDICAL PRODUCT FOR REDUCING BODY WEIGHT AND BODY FAT, AND USE OF SAID PRODUCT

FIELD OF THE INVENTION

The present invention relates to a composition, especially a composition comprises epigallocatechin gallate (EGCG), curcumin, and an excipient; the present invention relates to an application of said composition, especially an application in preparing a pharmaceutical composition for reducing body weight and body fat with said composition; the present invention relates to a pharmaceutical composition comprising said composition, especially a pharmaceutical composition for reducing body weight and body fat; the present invention further relates to an application of said pharmaceutical composition, especially an application for reducing body fat, reducing body weight, treating fatty liver, or treating non-alcoholic steatohepatitis with effective doses of said pharmaceutical composition.

BACKGROUND OF THE INVENTION

Obesity is a body condition in which accumulation of excessive body fat causes adverse effects on health, thereby potentially leading to shortened lifespan and various health problems. According to the definition of obesity by World Health Organization, a body mass index (BMI) greater than 25 is defined as overweight, and a BMI greater than 30 is defined as obese. Some Eastern Asian countries adopt stricter criteria. For example, the Ministry of Health and Welfare of Taiwan announced in April 2002 that a Taiwanese adult with BMI≥27 is considered obese, and 24≤BMI<27 is considered overweight.

The statistics show that the worldwide overweight and obese population has exceeded 2.7 billion people in 2014. Among them, approximately 13% are obese, and these obese people are at significantly higher risk of related diseases such as cardiovascular disease, hyperlipidemia, fatty liver, non-alcoholic steatohepatitis, cirrhosis, diabetes, and cancer.

Current synthetic drugs for reducing body fat or body weight still present cardiovascular risks and safety concerns to various extents. On the other hand, plant extract ingredients for reducing body fat or body weight often face the issue of low bioavailability and thus low efficacy. Therefore, the market is in dire need of a drug for reducing body fat and body weight with better safety profile, less side effects, no cardiovascular risks, and high bioavailability, that can effectively reduce body weight and body fat and lower the risks to cardiovascular disease.

SUMMARY OF THE INVENTION

Because of the drawback of the traditional art, the present invention provides a plant extract composition for reducing body weight and body fat. Said composition comprises green tea extract and turmeric extract, and the weight percentages of the green tea extract and the turmeric extract are 30% to 75% and 20% to 55%, respectively, based on the total weight of the plant extract composition. Alternatively, the weight percentages of the green tea extract and the turmeric extract are 20% to 91% and 9% to 80%, respectively, based on the total weight of the plant extract composition. Preferably, the weight percentages of the green tea extract and the turmeric extract are 40% to 67% and 33% to 60%, respectively.

Preferably, the weight ratio of the green tea extract to the turmeric extract in the plant extract composition is 1:4 to 10:1. Preferably, the weight ratio of the green tea extract to the turmeric extract is 2:3 to 2:1.

Preferably, the plant extract composition of the present invention further comprises resveratrol, and the resveratrol is greater than 0% by weight (hereinafter referred to as "wt %") and up to 30 wt % of the total weight of said composition.

In the present invention, turmeric extract refers to a mixture of turmeric ingredients extracted by any solvent and any extraction method, commercially available turmeric extract, any mixture containing more than 75 wt % curcumin, any mixture containing more than 75 wt % curcuminoid, or commercially available curcumin.

In the present invention, resveratrol refers to resveratrol extracted from natural plants or commercially available resveratrol. Preferably, the purity of resveratrol is 90% to 100% (in weight percentage).

In the present invention, green tea extract refers to a green tea ingredient mixture extracted by any solvent and any extraction method, or commercially available green tea extract. Preferably, it refers to a mixture containing at least 45 wt % epigallocatechin gallate (EGCG), any mixture containing at least 90 wt % catechins, or commercially available epigallocatechin gallate (EGCG).

Preferably, the weight percentages of catechins and curcumin are 20% to 91% and 9% to 80%, respectively, based on the total weight of the plant extract composition. Preferably, the weight percentages of catechins and curcumin are 40% to 67% and 33% to 60%, respectively.

Preferably, the weight ratio of catechins to curcumin in the plant extract composition is 1:4 to 10:1. Preferably, the weight ratio of catechins to curcumin is 2:3 to 2:1.

The present invention further provides a composition for reducing body weight or body fat, comprising:
  an excipient; and
  an active ingredient composition for reducing body weight or body fat, and the active pharmaceutical ingredient composition for reducing body weight or body fat comprises epigallocatechin gallate (EGCG) and curcumin
  Wherein, the excipient comprises at least one of glyceryl dibehenate, polyoxyethylene stearates, polysorbate 80 mixture, vitamin E polyethylene glycol succinate, glyceryl monostearate, and oleoyl polyoxyl-6 glycerides, or a combination thereof; additionally, the polysorbate 80 mixture comprises polysorbate 80 and magnesium aluminometasilicate.

Preferably, the composition for reducing body weight or body fat further comprises at least one of glyceryl palmitostearate, polysorbate 20, poloxamer, and polyethylene glycols (PEG), or a combination thereof.

Preferably, the composition for reducing body weight or body fat further comprises piperine.

Preferably, the polyoxyethylene stearate is polyoxyethylene (32) stearate, and the weight percentage of the polyoxyethylene (32) stearate is 0.1%-20% based on the total weight of the composition for reducing body weight or body fat; alternatively, the weight percentage of the polysorbate 80 mixture is 0.5%-20% based on the total weight of the composition for reducing body weight or body fat; alternatively, said polyoxyethylene stearate is polyoxyethylene (40) stearate, and the weight percentage of the polyoxyethylene (40) stearate is 0.005%-6.7% based on the total weight of the composition for reducing body weight or body fat.

Preferably, the polyoxyethylene stearate is polyoxyethylene (32) stearate, and the weight percentage of the polyoxyethylene (32) stearate is 1%-15% based on the total weight of the composition for reducing body weight or body fat; alternatively, the weight percentage of the polysorbate 80 mixture is 1%-15% based on the total weight of the composition for reducing body weight or body fat; alternatively, said polyoxyethylene stearate is polyoxyethylene (40) stearate, and the weight percentage of the polyoxyethylene (40) stearate is 0.01%-3.3% based on the total weight of the composition for reducing body weight or body fat.

Preferably, the polyoxyethylene stearate is polyoxyethylene (32) stearate, and the weight percentage of the polyoxyethylene (32) stearate is 1%-10% based on the total weight of the composition for reducing body weight or body fat; alternatively, the weight percentage of the polysorbate 80 mixture is 3%-10% based on the total weight of the composition for reducing body weight or body fat; alternatively, said polyoxyethylene stearate is polyoxyethylene (40) stearate, and the weight percentage of the polyoxyethylene (40) stearate is 0.05%-1% based on the total weight of the composition for reducing body weight or body fat.

Preferably, the polyoxyethylene stearate is polyoxyethylene (32) stearate, and the value of the ratio of the weight of the curcumin to the weight of the polyoxyethylene (32) stearate is 5.3-26.7; alternatively, the value of the ratio of the weight of the curcumin to the weight of the polysorbate 80 mixture is 2-8.9; alternatively, the polyoxyethylene stearate is polyoxyethylene (40) stearate, and the value of the ratio of the weight of the curcumin to the weight of the polyoxyethylene (40) stearate is 40-533.3; alternatively, the polyoxyethylene stearate is polyoxyethylene (32) stearate, and the value of the ratio of the weight of the active ingredient composition for reducing body weight or body fat to the weight of the polyoxyethylene (32) stearate is 9.5-47.5; alternatively, the value of the ratio of the weight of the active ingredient composition for reducing body weight or body fat to the weight of the polysorbate 80 mixture is 3.6-15.8; alternatively, the polyoxyethylene stearate is polyoxyethylene (40) stearate, and the value of the ratio of the weight of the active ingredient composition for reducing body weight or body fat to the weight of the polyoxyethylene (40) stearate is 71.3-950.

Preferably, the composition for reducing body weight or body fat further comprises at least one of mannitol, microcrystalline celluloses, sodium dodecyl sulfate (SDS), and cross-linked sodium carboxymethyl celluloses, or a combination thereof.

Preferably, the value of the ratio of the weight of the curcumin to the weight of the epigallocatechin gallate (EGCG) is 3.2-0.32; alternatively, the weight percentage of the epigallocatechin gallate (EGCG) is 23.8%-75.8%, and the weight percentage of the curcumin is 24.2%-76.2%, based on the total weight of the active ingredient composition for reducing body weight or body fat.

Preferably, the value of the ratio of the weight of the curcumin to the weight of the epigallocatechin gallate is 3.2-0.4; alternatively, the weight percentage of the epigallocatechin gallate is 23.8%-71.4%, and the weight percentage of the curcumin is 28.6%-76.2%, based on the total weight of the active ingredient composition for reducing body weight or body fat.

Preferably, the active ingredient composition for reducing body weight or body fat further comprises resveratrol.

The active ingredient composition for reducing body weight or body fat described in the present invention refers to a combination of at least two ingredients, each of which is able to reduce body weight or visceral fat of an individual when administered alone to the individual.

The present invention further provides a method for reducing body weight or body fat of an individual, comprising administering a composition to an individual, wherein the composition comprises
 an excipient; and
 an active ingredient composition for reducing body weight or body fat, and the active ingredient composition for reducing body weight or body fat comprises epigallocatechin gallate (EGCG) and curcumin
 Wherein, the excipient comprises at least one of glyceryl dibehenate, polyoxyethylene stearates, polysorbate 80 mixture, vitamin E polyethylene glycol succinate, glyceryl monostearate, and oleoyl polyoxyl-6 glycerides, or a combination thereof; additionally, the polysorbate 80 mixture comprises polysorbate 80 and magnesium aluminometasilicate.

Preferably, the composition further comprises at least one of glyceryl palmitostearate, polysorbate 20, poloxamer, and polyethylene glycols (PEG), or a combination thereof.

Preferably, the composition further comprises piperine.

Preferably, the polyoxyethylene stearate is polyoxyethylene (32) stearate, and the weight percentage of the polyoxyethylene (32) stearate is 0.1%-20% based on the total weight of the composition; alternatively, the weight percentage of the polysorbate 80 mixture is 0.5%-20% based on the total weight of the composition; alternatively, the polyoxyethylene stearate is polyoxyethylene (40) stearate, and the weight percentage of the polyoxyethylene (40) stearate is 0.005%-6.7% based on the total weight of the composition.

Preferably, the polyoxyethylene stearate is polyoxyethylene (32) stearate, and the weight percentage of the polyoxyethylene (32) stearate is 1%-15% based on the total weight of the composition; alternatively, the weight percentage of the polysorbate 80 mixture is 1%-15% based on the total weight of the composition; alternatively, the polyoxyethylene stearate is polyoxyethylene (40) stearate, and the weight percentage of the polyoxyethylene (40) stearate is 0.01%-3.3% based on the total weight of the composition.

Preferably, the polyoxyethylene stearate is polyoxyethylene (32) stearate, and the weight percentage of the polyoxyethylene (32) stearate is 1%-10% based on the total weight of the composition; alternatively, the polysorbate 80 mixture is 3%-10% based on the total weight of the composition; alternatively, the polyoxyethylene stearate is polyoxyethylene (40) stearate, and the weight percentage of the polyoxyethylene (40) stearate is 0.05%-1% based on the total weight of the composition.

Preferably, the polyoxyethylene stearate is polyoxyethylene (32) stearate, and the value of the ratio of the weight of the curcumin to the weight of the polyoxyethylene (32) stearate is 5.3-26.7; alternatively, the value of the ratio of the weight of the curcumin to the weight of the polysorbate 80 mixture is 2-8.9; alternatively, the polyoxyethylene stearate is polyoxyethylene (40) stearate, and the value of the ratio of the weight of the curcumin to the weight of the polyoxyethylene (40) stearate is 40-533.3; alternatively, the polyoxyethylene stearate is polyoxyethylene (32) stearate, and the value of the ratio of the weight of the active ingredient composition for reducing body weight or body fat to the weight of the polyoxyethylene (32) stearate is 9.5-47.5; alternatively, the value of the ratio of the weight of the active ingredient composition for reducing body weight or body fat to the weight of the polysorbate 80 mixture is 3.6-15.8; alternatively, the polyoxyethylene stearate is polyoxyethylene (40) stearate, and the value of the ratio of the weight of the active ingredient composition for reducing body weight or body fat to the weight of the polyoxyethylene (40) stearate is 71.3-950.

Preferably, wherein the composition further comprises at least one of mannitol, microcrystalline celluloses, sodium dodecyl sulfate, and cross-linked sodium carboxymethyl celluloses, or a combination thereof.

Preferably, the value of the ratio of the weight of the curcumin to the weight of the epigallocatechin gallate is 3.2-0.32; alternatively, the weight percentage of the epigallocatechin gallate is 23.8%-75.8%, and the weight percentage of the curcumin is 24.2%-76.2%, based on the total weight of the active ingredient composition for reducing body weight or body fat.

Preferably, the value of the ratio of the weight of the curcumin to the weight of the epigallocatechin gallate is 3.2-0.4; alternatively, the weight percentage of the epigallocatechin gallate is 23.8%-71.4%, and the weight percentage of the curcumin is 28.6%-76.2%, based on the total weight of the active ingredient composition for reducing body weight or body fat.

Preferably, the active ingredient composition for reducing body weight or body fat further comprises resveratrol.

Preferably, the composition is administered to the individual orally.

Preferably, the individual is an individual with normal body weight, an overweight individual, an obese individual, an individual with fatty liver, or an individual with non-alcoholic steatohepatitis (NASH).

The present invention further provides a method for treating fatty liver or non-alcoholic steatohepatitis, comprising administering a composition to an individual with fatty liver or non-alcoholic steatohepatitis, wherein the composition comprises an excipient; and an active ingredient composition for reducing body weight or body fat, and the active ingredient composition for reducing body weight or body fat comprises epigallocatechin gallate and curcumin;

wherein, the excipient comprises at least one of glyceryl dibehenate, polyoxyethylene stearates, polysorbate 80 mixture, vitamin E polyethylene glycol succinate, glyceryl monostearate, and oleoyl polyoxyl-6 glycerides, or a combination thereof; additionally, the polysorbate 80 mixture comprises polysorbate 80 and magnesium aluminometasilicate.

Preferably, the composition further comprises at least one of glyceryl palmitosterate, polysorbate 20, poloxamer, and polyethylene glycols, or a combination thereof.

Preferably, the composition further comprises piperine.

Preferably, the polyoxyethylene stearate is polyoxyethylene (32) stearate, and the weight percentage of the polyoxyethylene (32) stearate is 0.1%-20% based on the total weight of the composition; alternatively, the weight percentage of the polysorbate 80 mixture is 0.5%-20% based on the total weight of the composition; alternatively, the polyoxyethylene stearate is polyoxyethylene (40) stearate, and the weight percentage of the polyoxyethylene (40) stearate is 0.005%-6.7% based on the total weight of the composition.

Preferably, the polyoxyethylene stearate is polyoxyethylene (32) stearate, and the value of the ratio of the weight of the curcumin to the weight of the polyoxyethylene (32) stearate is 5.3-26.7; alternatively, the value of the ratio of the weight of the curcumin to the weight of the polysorbate 80 mixture is 2-8.9; alternatively, the polyoxyethylene stearate is polyoxyethylene (40) stearate, and the value of the ratio of the weight of the curcumin to the weight of the polyoxyethylene (40) stearate is 40-533.3; alternatively, the polyoxyethylene stearate is polyoxyethylene (32) stearate, and the value of the ratio of the weight of the active ingredient composition for reducing body weight or body fat to the weight of the polyoxyethylene (32) stearate is 9.5-47.5; alternatively, the value of the ratio of the weight of the active ingredient composition for reducing body weight or body fat to the weight of the polysorbate 80 mixture is 3.6-15.8; alternatively, the polyoxyethylene stearate is polyoxyethylene (40) stearate, and the value of the ratio of the weight of the active ingredient composition for reducing body weight or body fat to the weight of the polyoxyethylene (40) stearate is 71.3-950.

Preferably, wherein the composition further comprises at least one of mannitol, microcrystalline celluloses, sodium dodecyl sulfate, and cross-linked sodium carboxymethyl celluloses, or a combination thereof.

Preferably, the value of the ratio of the weight of the curcumin to the weight of the epigallocatechin gallate is 3.2-0.32; alternatively, the weight percentage of the epigallocatechin gallate is 23.8%-75.8%, and the weight percentage of the curcumin is 24.2%-76.2%, based on the total weight of the active ingredient composition for reducing body weight or body fat.

Preferably, the value of the ratio of the weight of the curcumin to the weight of the epigallocatechin gallate is 3.2-0.4; alternatively, the weight percentage of the epigallocatechin gallate is 23.8%-71.4%, and the weight percentage of the curcumin is 28.6%-76.2%, based on the total weight of the active ingredient composition for reducing body weight or body fat.

Preferably, the composition is administered orally to the individual with fatty liver or non-alcoholic steatohepatitis.

The present invention further provides a method for manufacturing a plant extract composition comprising green tea extract and turmeric extract, including mixing the plant extract composition comprising green tea extract and turmeric extract with a pharmaceutically acceptable salt composition, a pharmaceutically acceptable stabilizers or a pharmaceutically acceptable excipient to produce capsules, tablets, or to manufacture coated tablets or solutions for injection or infusion.

Preferably, the method further includes adding resveratrol to obtain a plant extract composition comprising green tea extract, turmeric extract, and resveratrol.

Preferably, the stabilizer includes, but is not limited to, xylitol, sorbitol, polydextrose, isomaltitol, and D-glucose.

The present invention further provides a use of said plant extract composition for reducing body weight and body fat in preparing a pharmaceutical composition for reducing body weight and body fat.

The present invention provides a pharmaceutical composition for reducing body weight and body fat comprising an effective dose of said plant extract composition for reducing body weight and body fat and a pharmaceutically acceptable excipient.

In the preferred embodiments, said pharmaceutical composition further comprises an effective dose of resveratrol for reducing body weight and body fat.

According to the present invention, said "pharmaceutically acceptable excipient" or "excipient" includes, but is not limited to, at least one of disintegrants, binders, fillers, lubricants, suspending agents, solubilizers, and glidants.

Preferably, said pharmaceutically acceptable excipient or excipient includes, but is not limited to, at least one of piperine, glyceryl dibehenate (also known as glyceryl monobehenate, the main ingredient of Compritol 888 ATO), oleoyl polyoxyl-6 glycerides (also known as oleoyl macrogolglycerides, the main ingredient of Labrafil M 1944 CS), glycerol palmitostearate (the main ingredient of Precirol ATO 5), magnesium stearate, poloxamer 188, Labrasol, Poloxamer 407, polyethylene glycol 6000 (PEG 6000), glyceryl monostearate (the main ingredient of IMWITOR 491), sodium dodecyl sulfate (SDS), Sepitrap 80 (a polysorbate 80 mixture, comprising polysorbate 80 and magnesium aluminometasilicate), polyethylene glycol 400 (PEG 400), polysorbate 20, polyoxyethylene stearates, polyoxyethylene (32) stearate (the main ingredient of Gelucire® 48/16), polyoxyethylene (40) stearate, and vitamin E polyethylene glycol succinate (the main ingredient of TPGS), or a combination thereof. The amount of excipient used depends on the amount of active ingredient used and the formulation, and one type of excipient can perform more than one function.

Preferably, in the embodiments of the present invention where glyceryl dibehenate was added refers to examples such as directly adding glyceryl dibehenate or adding Compritol 888 ATO; in the embodiments of the present invention where oleoyl polyoxyl-6 glycerides were added refers to examples such as directly adding oleoyl polyoxyl-6 glycerides or adding Labrafil M 1944 CS; in the embodiments of the present invention where glyceryl palmitostearate was added refers to examples such as directly adding glyceryl palmitostearate or adding Precirol ATO 5; in the embodiments of the present invention where glyceryl monostearate was added refers to examples such as directly adding glyceryl monostearate or adding IMWITOR 491; in the embodiments of the present invention where polysorbate 80 mixture was added refers to examples such as adding any mixture comprising polysorbate 80 and magnesium aluminometasilicate or adding Sepitrap 80; in the embodiments of the present invention where polyoxyethylene (32) stearate was added refers to examples such as directly adding polyoxyethylene (32) stearate or adding Gelucire® 48/16; in the embodiments where vitamin E polyethylene glycol succinate was added refers to examples such as directly adding vitamin E polyethylene glycol succinate or adding TPGS.

Preferably, based on the total weight of the composition, the weight percentage of excipient is 10%-60%.

Preferably, based on the total weight of the composition, the weight percentage of piperine is 0.1%-1%.

Preferably, based on the total weight of the composition, the weight percentage of glyceryl dibehenate is 1%-10%. Preferably, the weight percentage of glyceryl dibehenate is 1%-3%.

Preferably, based on the total weight of the composition, the weight percentage of oleoyl macrogolglycerides is 10%-99%.

Preferably, based on the total weight of the composition, the weight percentage of glyceryl palmitostearate is 1%-3%.

Preferably, based on the total weight of the composition, the weight percentage of magnesium stearate is 0%-2%. Preferably, the weight percentage of magnesium stearate is 0%-0.5%.

Preferably, based on the total weight of the composition, the weight percentage of poloxamer 188 is 0.01%-10%.

Preferably, based on the total weight of the composition, the weight percentage of poloxamer 407 is 0.01%-10%.

Preferably, based on the total weight of the composition, the weight percentage of Labrasol is 10%-99%. Preferably, the weight percentage of Labrasol is 10%-35%.

Preferably, based on the total weight of the composition, the weight percentage of PEG 6000 is 0%-5%.

Preferably, based on the total weight of the composition, the weight percentage of IMWITOR 491 is 0.5%-2%.

Preferably, based on the total weight of the composition, the weight percentage of sodium dodecyl sulfate is 0.5%-2.5%.

Preferably, based on the total weight of the composition, the weight percentage of Sepitrap 80 is 0%-20%.

Preferably, said disintegrant includes at least one of agar, alginic acid, calcium carbonate, carboxymethylcelluloses, celluloses, clays, colloidal silica, croscarmellose sodium, cross-linked providone, gum, magnesium aluminum silicate, methyl celluloses, polacrilin potassium, sodium alginate, low substituted hydroxypropyl cellulose, crosslinked polyvinylpyrrolidone hydroxypropylcelluloses, sodium starch glycolate, starch, cross-linked sodium carboxymethyl celluloses, cross-linked polyvinylpyrrolidone (also known as polyvinylpolypyrrolidone, PVPP), and L-hydroxypropyl cellulose (L-HPC) or a combination thereof.

Preferably, said binder includes, but is not limited to, microcrystalline cellulose (MCC), hydroxymethyl cellulose, hydroxypropyl cellulose, water, ethanol, hydroxypropyl methylcellulose, polyvinylpyrrolidone (also known as povidone; PVP-K series), carboxymethylcellulose, Tween series, SPAN series, Vitamin E TPGS, Gelucire® 48/16, polyethylene glycol (PEG), propylene glycol, hydroxypropyl methylcellulose, and cyclodextrin series.

Preferably, said filler includes at least one of calcium carbonate, calcium phosphate, dibasic calcium phosphate, calcium sulfate, calcium carboxymethylcelluloses, celluloses, dextrin, salt, dextrose, fructose, lactitol, lactose, carbonate, magnesium oxide, maltitol, maltodextrin, maltose, sorbitol, starch, sucrose, sugar, xylitol, mannitol, glucose, powdered celluloses, and microcrystalline celluloses, or a combination thereof.

Preferably, said lubricant includes, but is not limited to, agar, calcium stearate, ethyl oleate, ethyl laurate, glycerin, glyceryl palmitostearate, hydrogenated vegetable oil, magnesium oxide, magnesium stearate, mannitol, poloxamer, ethylene glycol, sodium benzoate, sodium lauryl sulfate, sodium stearate, sorbitol, stearic acid, talc, zinc stearate, silicon dioxide, and talc powder.

Preferably, said suspending agent includes, but is not limited to, mannitol, carboxymethyl cellulose (CMC), and CMC-Na. Preferably, said solubilizer includes, but is not limited to, at least one of hydroxypropyl-beta-cyclodextrin, Tween 80, castor oil, polyethylene glycol (PEG), poloxamer, polysorbate, sorbitan fatty acid esters (the main ingredients of the commercial product Span), vitamin E polyethylene glycol succinate (the main ingredient of TPGS), polyoxyethylene stearates, propylene glycol, glyceryl stearate, and Sepitrap 80, or a combination thereof.

Preferably, said glidant includes, but is not limited to, materials such as magnesium stearate, silicon dioxide, magnesium trisillicate, powdered cellulose, starch, talc, tribasic calcium phosphate, calcium silicate, magnesium silicate, colloidal silicon dioxide, and silicon hydrogel.

Said pharmaceutical composition of the present invention may exist in various formulations. These formulations include, but are not limited to, liquid, semi-solid, and solid pharmaceutical formulation, such as liquid solution (for example, solution for injection and solution for infusion), dispersion, suspension, tablet, pill, powder, liposome, and suppository. The preferred formulation depends on the expected route of administration and treatment application. Preferably, the pharmaceutical composition of the present invention is presented in orally available formulation or a formulation which can be injected or infused. In the embodiments of the present invention, the pharmaceutical composition for reducing body weight and body fat comprising effective dose of the composition of green tea extract and turmeric extract is administered orally. The suitable and preferred oral formulations of the plant extract composition according to the present invention include pill, granule, coated tablet, capsule, and tablet, and other solid oral formulations are also within the scope of the present invention.

The preparation method of said soft capsule described in the present invention is as follows: mixing green tea extract and curcumin in appropriate lipid excipients (such as lecithin, beeswax, coconut oil, and palm oil, etc.) to form an oily solution comprising the ingredients; conducting a soft capsule filling process to encapsulate and mold the oily solution comprising the ingredients into a capsule membrane material in liquid form (for example, gelatin, glycerol, or water, etc.), alternatively, making animal gelatin into thin layers and processing them into the outer membrane of capsules with stainless steel molds, and filling the oily solution comprising the ingredients into the outer membrane; drying the soft capsules and conducting sorting and packaging processes.

The present invention further provides an application for reducing body weight and body fat using said pharmaceutical composition, which achieves the effect of reducing body fat and body weight by administering effective doses of the pharmaceutical composition comprising the plant extract composition comprising green tea extract and turmeric extract to a recipient, and the recipient is a human or an animal.

Preferably, the administration is oral administration or injection administration.

Preferably, the effective dose is 1.8 mg to 145 mg of the pharmaceutical composition per day per kg of a recipient, and the recipient is a human or an animal. Preferably, the recipient is a human.

Preferably, the effective dose is 5.4 mg to 70 mg of the pharmaceutical composition per day per kg of a recipient, and the recipient is a human or an animal. Preferably, the recipient is a human.

In the present invention, "effective dose" herein refers to the effective dose calculated for different recipients based on Table 1 in "Estimating the maximum safe starting dose in initial clinical trials for therapeutics in adult healthy volunteers" published by the US Food and Drug Administration (FDA).

In the present invention, "reducing body weight and body fat" refers to the reduction of indices such as body weight or body fat of an individual as compared to the obesity control group after administration of effective doses of the composition comprising green tea extract and turmeric extract or the composition further comprising resveratrol. Reduction of body fat can be determined through administering an amount within a specific range of the composition comprising green tea extract and turmeric extract or the composition further comprising resveratrol, and measuring the change of the amount of fat, such as epididymal fat, perirenal fat, mesenteric fat, or groin and extraperitoneal fat within a specific time frame.

The ingredients of the plant extract composition of the present invention are all extracted from plants. Experimental results demonstrate that said plant extract composition described in the present invention does not affect appetite or the amount of food intake, nor does it affect other safety of serum biochemistry indicators, and thus it has a better safety profile; comparing to other weight loss drugs on the market, it is also safer and has no apparent side effects. Moreover, comparing to the methods of the prior art that reduce body weight by decreasing calorie uptake through inhibiting appetite or blocking intestinal fat absorption, said plant extract composition described in the present invention not only can reduce body weight, but also can effectively inhibit the proliferation of adipocytes, increase fat metabolism and energy expenditure, and target the fundamental causes of obesity to ameliorate the issue of weight regain after weight loss and improve various cardiovascular risk indicators such as blood lipid and blood sugar, etc. to reduce cardiovascular risk.

Therefore, said plant extract composition described in the present invention provides a safer and more effective method for reducing body weight and body fat against the global obesity and overweight epidemic, and may be applied to the use of related pharmaceutical compositions or dietary supplements in the future.

DETAILED DESCRIPTION OF THE INVENTION

The technical solutions to achieve the predetermined objectives of the present invention are further described hereinafter with the accompanying drawings and the preferred embodiments of the present invention.

Example 1. Preadipocyte Growth Inhibition Experiment

In this embodiment, 3T3-L1 preadipocytes were plated at the density of $1\times10^4$ cells/well in 96-well plates. With the exception of controls (that is, the DMSO vehicle control group), different wells were respectively added with 50 ppm of resveratrol, 50 ppm of turmeric extract, 80 ppm of green tea extract, and 100 ppm of the plant extract compositions ME008A, ME008D, ME001, ME00C1, and ME00D1 of the present invention. The experiment was composed of nine groups with three replicates per group. After addition of the drugs and forty-eight hours of incubation, the growth condition of cells was imaged and recorded, and the growth inhibitory effect of each test substance on 3T3-L1 preadipocytes was analyzed by MTT assay. Wherein, each test substance was prepared in DMSO or sterile water. The plant extract composition ME008A of the present invention comprised 50 wt % green tea extract, 25 wt % green coffee bean extract, and 25 wt % resveratrol; ME008D comprised 40 wt % green tea extract, 45 wt % green coffee bean extract, and 15 wt % resveratrol; ME001 comprised 60 wt % green tea extract, 10 wt % turmeric extract, and 30 wt % resveratrol; ME00C1 comprised 40 wt % green tea extract, 50 wt % turmeric extract, and 10 wt % resveratrol; ME00D1 comprised 75 wt % green tea extract and 25 wt % turmeric extract. The data of each group are expressed as mean±SD. Letters a, b, c, d, e, f, and g indicate the results of statistical analysis, wherein different letters indicate significant statistical difference between groups ($p<0.05$), and identical letters indicate no significant statistical difference between groups ($p>0.05$).

Figure 1:
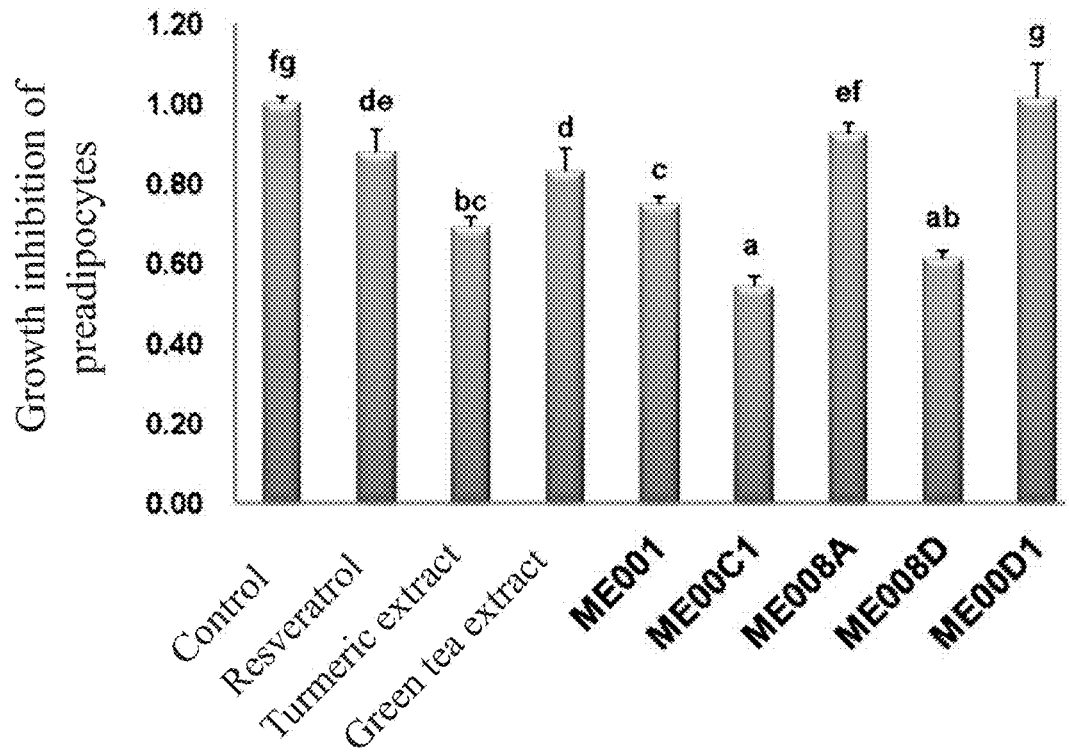
FIG. 1 is a bar graph showing the inhibitory effect of each group of the present invention on the growth of preadipocyte tested by MTT assay.

Results are shown in FIG. 1. Comparing to the control group, three groups of plant extract compositions ME00C1, ME001, and ME008D of the present invention all significantly inhibited the growth of preadipocytes ($p<0.05$). Among them, ME00C1 demonstrated the best growth inhibitory effect on preadipocytes ($p<0.05$), and the growth inhibitory effect of the ME00C1 composition on preadipocytes was significantly better than that of resveratrol, turmeric extract, or green tea extract administered alone ($p<0.05$).

Example 2. Differentiating Adipocyte Growth Inhibition Experiment

In this embodiment, 3T3-L1 preadipocytes were plated at a density of $1\times10^5$ cells/well in 12-well plates. On day four of culture, the medium was replaced with medium comprising 5 μg/ml of the differentiation inducer insulin, 1 μM of dexamethasone, and 0.5 mM of 3-isobutyl-1-methylxanthine to induce adipocyte differentiation. With the exception of the control group (that is, the DMSO vehicle control group), each group was respectively added with 50 ppm of resveratrol, 50 ppm of turmeric extract, 80 ppm of green tea extract, and 100 ppm of the plant extract compositions ME008A, ME008D, ME001, ME00C1, and ME00D1 of the present invention for experimentation. The experiment was composed of nine groups with three replicates per group. After addition of the drugs and forty-eight hours of incubation, the growth situation of cells was imaged and recorded, and the inhibitory effect of each test substance on differentiating adipocytes was analyzed by MTT assay. The data of each group are expressed as mean±SD. Letters a, b, c, d, e, and f indicate the results of statistical analysis, wherein different letters indicate significant statistical difference between groups ($p<0.05$), and identical letters indicate no significant statistical difference between groups ($p>0.05$).

Figure 2:
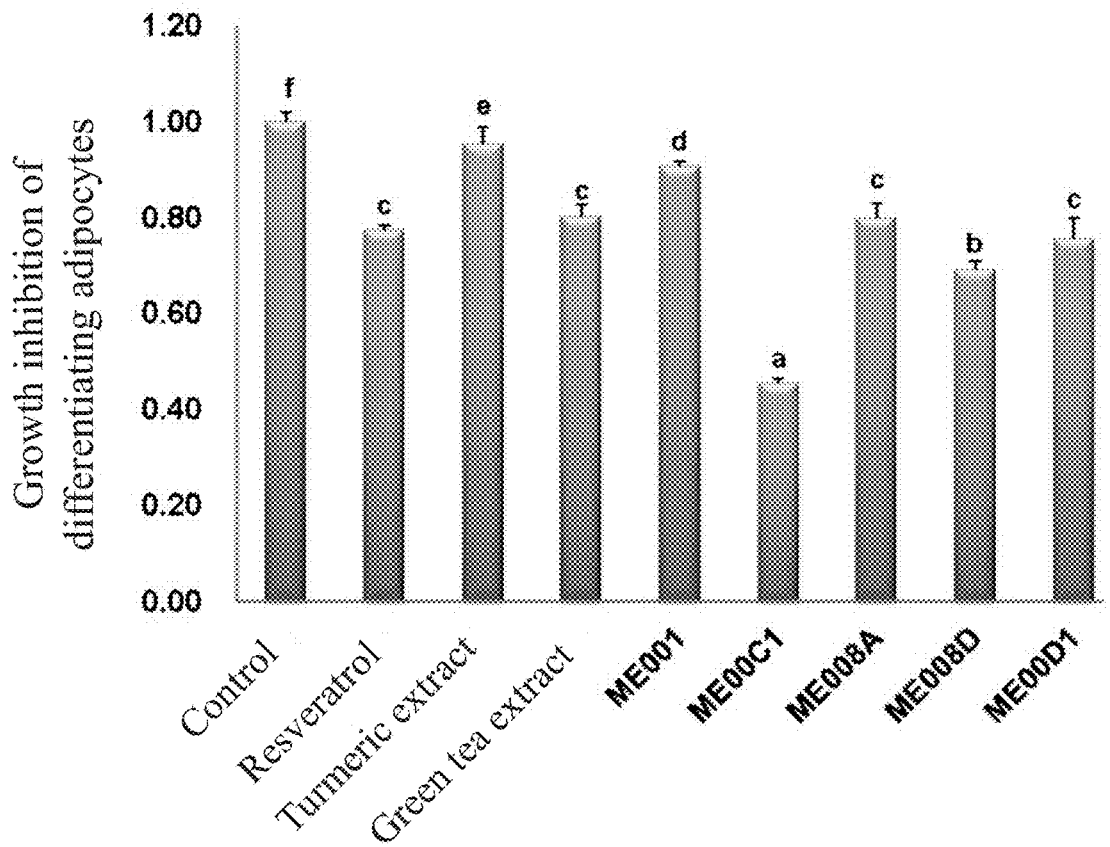
FIG. 2 is a bar graph showing the inhibitory effect of each group of the present invention on the growth of differentiating adipocytes tested by MTT assay.

Results are shown in FIG. 2. Comparing to the control group, every plant extract composition of the present invention significantly inhibited the growth of differentiating adipocytes ($p<0.05$). Among them, ME00C1 demonstrated the best growth inhibitory effect on differentiating adipocytes (p<0.05), and the growth inhibitory effect on differentiating adipocyte of the composition ME00C1 was significantly better than that of resveratrol, turmeric extract, or green tea extract administered alone (p<0.05).

Example 3. Gene Expression Level of Hormone Sensitive Lipase in Mature Adipocytes Experiment In this embodiment, 3T3-L1 cells were plated at a density of $3 \times 10^4$ cells/well in 12-well plates. On day four of culturing, the medium was replaced with DMEM medium (Gibco Inc, Germany) comprising 5 µg/ml of insulin, 1 µM of dexamethasone, and 0.5 mM of 3-isobutyl-1-methylxanthine. After two days of culturing, the medium was replaced with medium comprising 5 µg/ml of insulin and cultured for another 6 days. Once 3T3-L1 cells were differentiated and matured, with the exception of the control group (that is, the DMSO vehicle control group), each group was respectively added with 50 ppm of turmeric extract, 50 ppm of green tea extract, and 50 ppm of plant extract compositions of the present invention C15, C14, C13, C12, C11, D11, D12, D13, D14, and D15 for experimentation. The experiment was composed of thirteen groups with three replicates per group. Wherein, please refer to Table 1, the plant extract composition C15 of the present invention comprised 20 wt % green tea extract and 80 wt % turmeric extract, C14 comprised 33 wt % green tea extract and 67 wt % turmeric extract, C13 comprised 40 wt % green tea extract and 60 wt % turmeric extract, C12 comprised 50 wt % green tea extract and 50 wt % turmeric extract, C11 comprised 60 wt % green tea extract and 40 wt % turmeric extract, D11 comprised 67 wt % green tea extract and 33 wt % turmeric extract, D12 comprised 75 wt % green tea extract and 25 wt % turmeric extract, D13 comprised 80 wt % green tea extract and 20 wt % turmeric extract, D14 comprised 83 wt % green tea extract and 17 wt % turmeric extract, and D15 comprised 91 wt % green tea extract and 9 wt % turmeric extract. After addition of the drugs and seventy-two hours of incubation, RNA of the mature adipocytes was extracted by Trizol reagent (Thermo Fisher Scientific Inc, USA), and RT-PCR was carried out using a reverse transcription kit (Thermo Fisher Scientific Inc, USA) and a polymerase chain reaction kit (Thermo Fisher Scientific Inc, USA) to measure the expression level of hormone sensitive lipase (HSL) in mature adipocytes. Wherein, the primers for PCR reaction were 5'-GAATAT-CACGGAGATCGAGG-3' and 5'-CCGAAGGGACACG-GTGATGC-3'. The data of each group are expressed as mean±SD. Letters a, b, c, and d indicate the results of statistical analysis, wherein different letters indicate significant statistical difference between groups (p<0.05), and identical letters indicate no significant statistical difference between groups (p>0.05).

Figure 3:
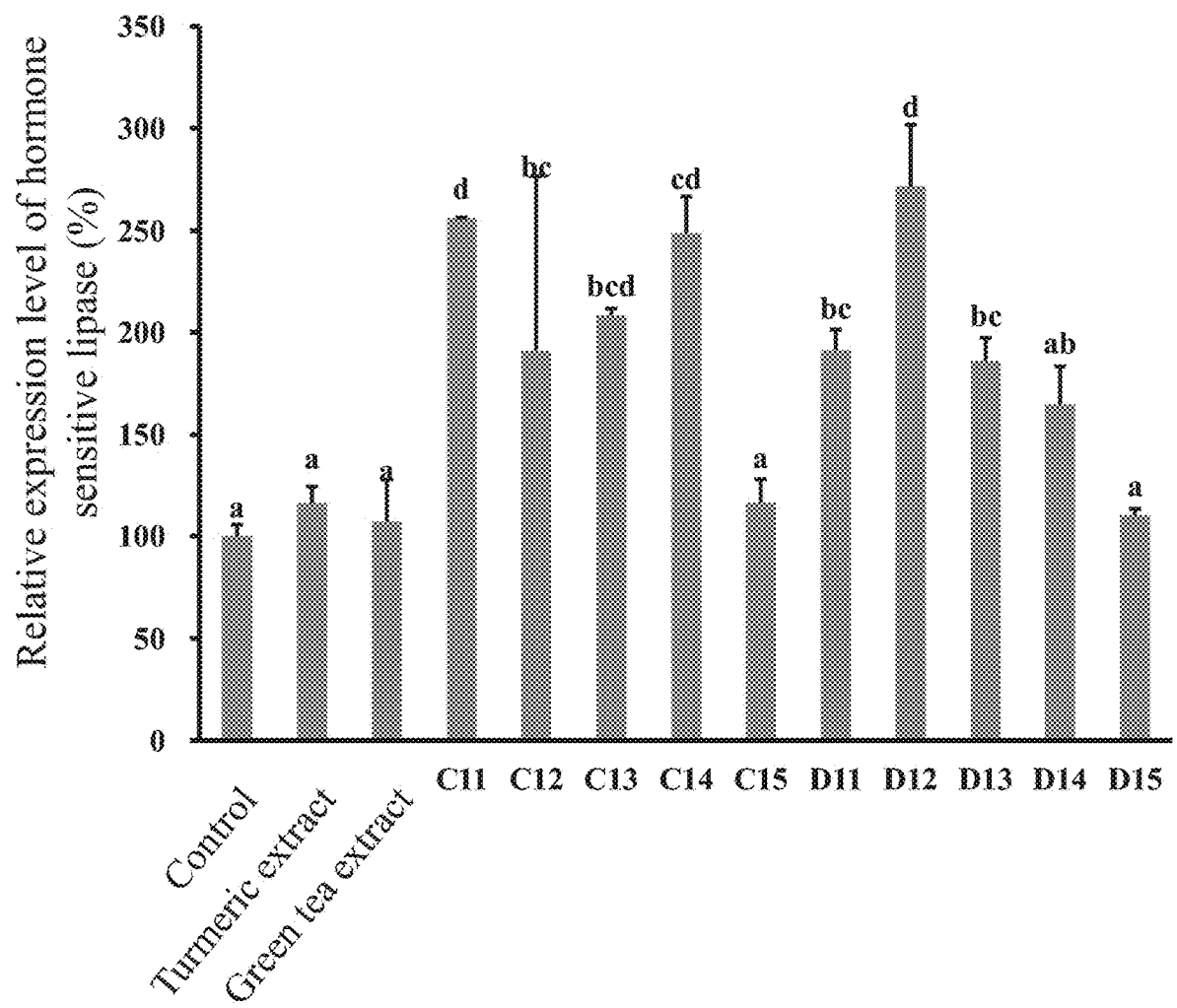
FIG. 3 is a bar graph showing the expression of lipase in mature adipocytes of each group tested by reverse transcription polymerase chain reaction (RT-PCR).

The results are shown in FIG. 3. Comparing to the control group, the turmeric extract group, and the green tea extract group, the plant extract compositions C11, C12, C13, C14, D11, D12, and D13 of the present invention all significantly increased the expression level of hormone sensitive lipase (p<0.05), and showed synergistic effects on increasing the expression level of hormone sensitive lipase, demonstrating an unanticipated effect. Therefore, synergy is achieved when the ratio of the weight of green tea extract to the weight of turmeric extract is 1:2-4:1; that is, synergy is achieved when the ratio of the weight of green tea extract to the weight of turmeric extract is 0.5-4. That is, synergy is achieved when the ratio of the weight of turmeric extract to the weight of green tea extract is 0.25-2. The turmeric extract used in the embodiments of the present invention comprises at least 80% curcumin, and the green tea extract used contains at least 50% epigallocatechin gallate. Therefore, based on the conversion of results of this embodiment, synergy is achieved when the ratio of the weight of curcumin to the weight of epigallocatechin gallate is 0.4-3.2, provided that the weight percentages of curcumin is 28.57%-76.19% and the weight percentages of epigallocatechin gallate is 23.81%-71.43%.

TABLE 1

| Group | Ratio between green tea extract and turmeric extract (Weight ratio) | Administered concentration (ppm) of plant extract composition |
|---|---|---|
| Control group | Ctrl | — |
| Curcumin (Cur.) | Cur. | 50 |
| Green tea (Gre.) | Gre. | 50 |
| C11 | 3:2 | 50 |
| C12 | 1:1 | 50 |
| C13 | 2:3 | 50 |
| C14 | 1:2 | 50 |
| C15 | 1:4 | 50 |
| D11 | 2:1 | 50 |
| D12 | 3:1 | 50 |
| D13 | 4:1 | 50 |
| D14 | 5:1 | 50 |
| D15 | 10:1 | 50 |

Example 4. Animal Experiment I (Drug Administration During Obesity Induction)

In this experimental example, 8-week old B6 female mice were experimented and divided into a normal control group, an obesity control group, a resveratrol group (the administered dose of resveratrol was 61.5 mg/kg B.W.), a green tea extract group (the administered dose of green tea extract was 123 mg/kg B.W.), and the plant extract compositions ME001 of the present invention group (the administered dose of ME001 was 676.5 mg/kg B.W.) Five female mice were included in each group for experimentation. During the experimental period, with the exception of the normal control group, the other groups were fed with high-fat diet for eight consecutive weeks to induce obesity symptoms, and were also fed by oral gavage with the test substance daily during the same eight weeks. The obesity control group was fed by oral gavage with an equal volume of sterile water, and the difference in body weight of each group of mice was evaluated. The body weight and average food intake of each animal were recorded weekly during the experimental period. The mice were sacrificed after the experimentation. During the experimental period of this experiment, no statistical difference (p>0.05) was observed in the weekly average food intake among the groups of mice fed with high-fat diet. The data of each group are expressed as mean±SD. Letters a, b, and c indicate the results of statistical analysis, wherein different letters indicate significant statistical difference between groups (p<0.05), and identical letters indicate no significant statistical difference between groups (p>0.05).

Figure 4:
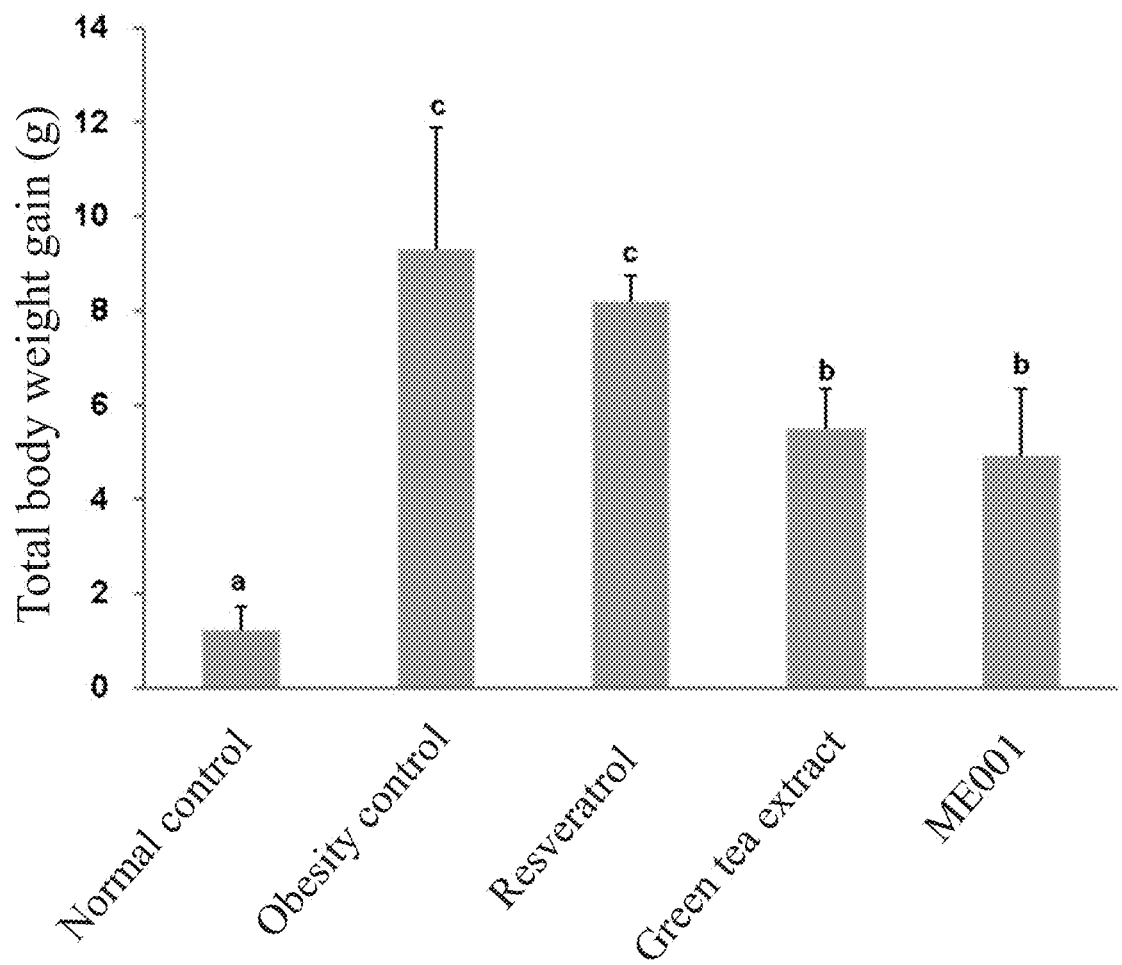
FIG. 4 is a bar graph showing the difference in body weight gain of each group of mice tested by administering drugs during obesity induction.

The experimental results are shown in FIG. 4. Comparing to the obesity control group, the total body weight gain of mice fed with the plant extract composition ME001 of the present invention was significantly reduced (p<0.05), and the extent of reduction was 47.2%. Therefore, the plant extract composition ME001 of the present invention can effectively achieve the effect of reducing body weight (p<0.05). On the contrary, the total body weight gain of mice in the group administered with resveratrol alone did not show statistical difference (p>0.05) comparing to that of the obesity control group.

Additionally, comparing to the other groups, the plant extract composition ME001 of the present invention not only effectively reduced body weight, but its efficacy was better than the groups of single plant extract (p<0.05), demonstrating its superior efficacy in reducing body weight.

Example 5. Dissolution Testing I (the Effect of Different Excipients on the Dissolution Rate of Curcumin)

In order to test the effect of excipients on the dissolution rate of curcumin in the composition of the present invention in the digestive tract of individuals, the inventor performed the following dissolution test.

The test substances of this experiment were prepared as follows:

Preparing tablets comprising 1% polyoxyethylene (32) stearate: 250 mg of green tea extract, 200 mg of turmeric extract, polyoxyethylene (32) stearate, fillers, and disintegrants were added in order into a mixer for mixing, and the dry powder was compressed into tablets to obtain tablets comprising 1% polyoxyethylene (32) stearate. The weight of each tablet comprising 1% polyoxyethylene (32) stearate was 600 mg, and each tablet comprising 1% polyoxyethylene (32) stearate comprised 250 mg of green tea extract, 200 mg of turmeric extract, and 1 wt % polyoxyethylene (32) stearate.

Preparing tablets comprising 5% polysorbate 80 mixture: the preparation method was roughly the same as that of tablets comprising polyoxyethylene (32) stearate. The only difference was that 5% polysorbate 80 mixture was used to substitute for polyoxyethylene (32) stearate, such that each tablet comprised 5 wt % polysorbate 80 mixture. Wherein, said polysorbate 80 mixture was Sepitrap 80.

Preparing tablets comprising 0.5% polyoxyethylene (40) stearate, tablets comprising 3% vitamin E polyethylene glycol succinate, tablets comprising 5% polysorbate 20, tablets comprising 1% polyethylene glycol (PEG) 400, tablets comprising 1% polyethylene glycol (PEG) 6000, tablets comprising 1% glyceryl monostearate, tablets comprising 1% oleoyl polyoxyl-6 glycerides, or tablets comprising 1% glyceryl dibehenate: the preparation methods were roughly the same as that of tablets comprising 1% polyoxyethylene (32) stearate. The only difference was that polyoxyethylene (40) stearate, vitamin E polyethylene glycol succinate, polysorbate 20, PEG 400, PEG 600, glyceryl monostearate, oleoyl polyoxyl-6 glycerides, or glyceryl dibehenate was used to substitute for polyoxyethylene (32) stearate, respectively, such that each tablet comprised 0.5 wt % polyoxyethylene (40) stearate, 3 wt % vitamin E polyethylene glycol succinate, 5 wt % polysorbate 20, 1 wt % PEG 400, 1 wt % PEG 6000.1 wt % glyceryl monostearate, 1 wt % oleoyl polyoxyl-6 glycerides, or 1 wt % glyceryl dibehenate, respectively.

Preparing control group tablets: the preparation method was roughly the same as that of tablets comprising polyoxyethylene (32) stearate. The only difference was that polyoxyethylene (32) stearate was omitted.

In all of the aforementioned tablets, each tablet comprised 250 mg of green tea extract and 200 mg of turmeric extract, each tablet weighed 600 mg, and the fillers, the disintegrants, and the binders used in the preparation procedure of each tablet were identical.

The fillers described in this embodiment comprised at least one of mannitol, starch, glucose, lactose, maltodextrin, dextrin, microcrystalline cellulose, sucrose, maltose, calcium carbonate, and powdered cellulose, or a combination thereof.

The disintegrants described in this embodiment comprised at least one of cross-linked sodium carboxymethyl cellulose, cross-linked polyvinylpyrrolidone, and low-substituted hydroxypropyl cellulose, or a combination thereof.

A tablet was individually placed into a dissolution medium in a dissolution instrument (Apparatus 2, manufactured by SMI-LabHut Ltd, UK). The dissolution medium was 0.1N hydrochloric acid (HCl), the volume of the dissolution medium was 900 ml, comprising 4% SDS, and the temperature was 37±0.5° C. The dissolution test was performed at a rotational speed of 100 rpm. Samples were collected at 30 minutes and 60 minutes of testing. The curcumin concentration in the samples was measured by high performance liquid chromatography (HPLC), and the dissolution rate of curcumin was calculated by the following method:

The total weight (grams) of dissolved curcumin in the dissolution medium÷the total weight (grams) of curcumin in a tablet=the dissolution rate of curcumin According to the criteria for dissolution testing of oral dosage forms by the US FDA, the dissolved amount of slowly dissolving or sparingly water-soluble drugs should be no less than 85% of the labeled amount. Therefore, if the dissolution rate of curcumin from a tablet at 30 minutes or 60 minutes of dissolution testing is at least 85%, the tablet meets the criteria for oral dosage forms. Wherein, if the dissolution rate of curcumin in the tablet is at least 85% at 30 minutes of dissolution testing, it is referred to as rapidly dissolving.

After duplication of this experiment, it was found that the difference between duplicated experimental results was less than 1% for each type of tablets.

Figure 5:
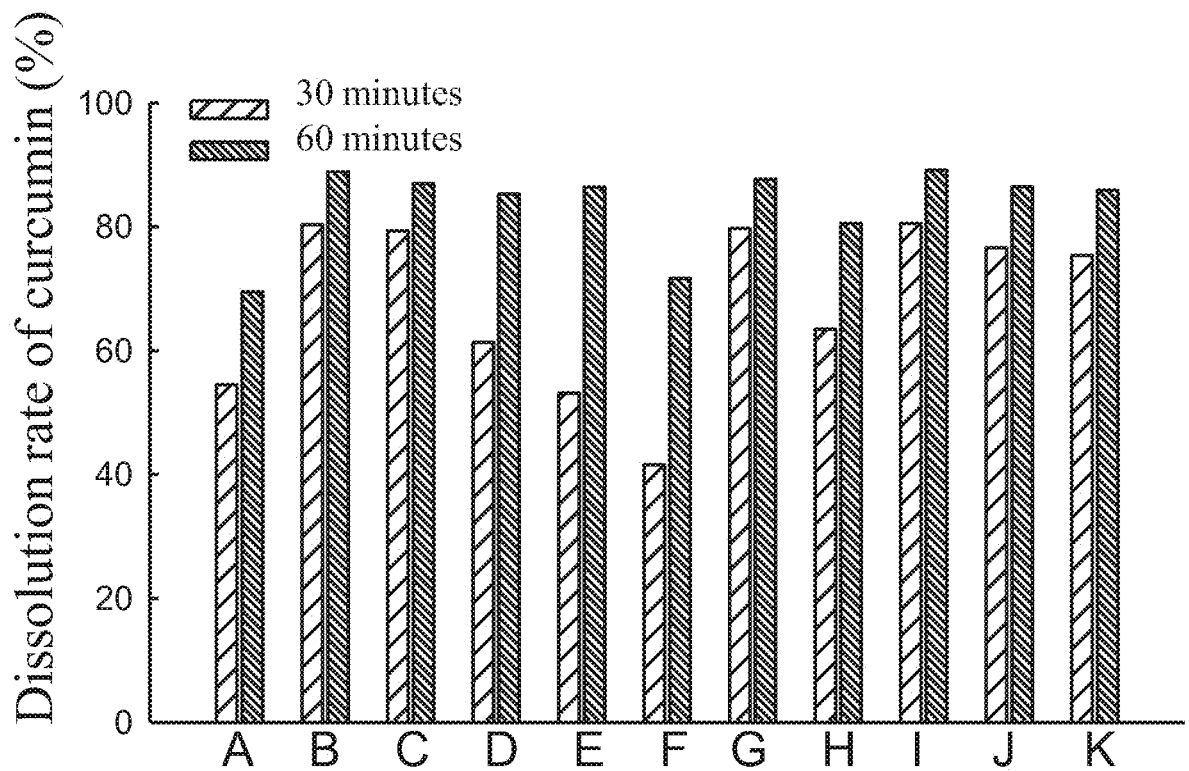
FIG. 5 is a bar graph showing the effect of different excipients on the dissolution rate of curcumin in the composition of the present invention tested by dissolution testing.

The testing results are shown in FIG. 5. The dissolution rate of curcumin in the control group tablets, the tablets comprising 1% polyoxyethylene (32) stearate, the tablets comprising 0.5% polyoxyethylene (40) stearate, the tablets comprising 5% polysorbate 80 mixture, the tablets comprising 3% vitamin E polyethylene glycol succinate, the tablets comprising 5% polysorbate 20, the tablets comprising 1% PEG 400, tablets comprising 1% PEG 6000, the tablets comprising 1% glyceryl monostearate, the tablets comprising 1% oleoyl polyoxyl-6 glycerides, and the tablets comprising 1% glyceryl dibehenate at 30 minutes was respectively 54.48%, 80.35%, 79.36%, 61.36%, 53.12%, 41.57%, 79.75%, 63.46%, 80.50%, 76.62%, and 75.36%, where none reached 85%; however, among them, the dissolution rate of the tablets comprising 1% polyoxyethylene (32) stearate, the tablets comprising 0.5% polyoxyethylene (40) stearate, the tablets comprising 1% PEG 400, and the tablets comprising 1% glyceryl monostearate was the highest, where all of which was at 80±1%.

Therefore, polyoxyethylene (32) stearate, polyoxyethylene (40) stearate, PEG 400, and glyceryl monostearate can all make the composition comprising epigallocatechin gallate and curcumin in the present invention almost meet the criteria of rapid dissolving.

Please continue to refer to FIG. 5. The dissolution rate of curcumin from the control group tablets, the tablets comprising 1% polyoxyethylene (32) stearate, the tablets comprising 0.5% polyoxyethylene (40) stearate, the tablets comprising 5% polysorbate 80 mixture, the tablets comprising 3% vitamin E polyethylene glycol succinate, the tablets comprising 5% polysorbate 20, the tablets comprising 1% PEG 400, the tablets comprising 1% PEG 6000, the tablets comprising 1% glyceryl monostearate, the tablets comprising 1% oleoyl polyoxyl-6 glycerides, and the tablets comprising 1% glyceryl dibehenate at 60 minutes was respectively 69.50%, 89.01%, 86.97%, 85.30%, 86.41%, 71.67%, 87.68%, 80.52%, 89.14%, 86.50%, and 85.89%.

Wherein, the dissolution rate curcumin from the tablets comprising 1% polyoxyethylene (32) stearate, the tablets comprising 0.5% polyoxyethylene (40) stearate, the tablets comprising 5% polysorbate 80 mixture, the tablets comprising 3% vitamin E polyethylene glycol succinate, the tablets comprising 1% PEG 400, the tablets comprising 1% glyceryl monostearate, the tablets comprising 1% oleoyl polyoxyl-6 glycerides, and the tablets comprising 1% glyceryl dibehenate at 60 minutes was greater than 85%.

Therefore, polyoxyethylene (32) stearate, polyoxyethylene (40) stearate, 5% polysorbate 80 mixture, vitamin E polyethylene glycol succinate, PEG 400, glyceryl monostearate, oleoyl polyoxyl-6 glycerides, and glyceryl dibehenate can all make the composition comprising epigallocatechin gallate and curcumin of the present invention meet the criteria for oral dosage forms and promote the bioavailability.

Example 6. Dissolution Testing II (the Effect of Different Concentrations of Excipients on the Dissolution Rate of Curcumin)

Example 6-1. The Effect of Different Concentrations of Polyoxyethylene (40) Stearate on the Dissolution Rate of Curcumin Preparing tablets comprising 0.5% polyoxyethylene (40) stearate: the preparation method was the same as that of tablets comprising 0.5% polyoxyethylene (40) stearate in Example 5.

Preparing tablets comprising 0.05% polyoxyethylene (40) stearate, or tablets comprising 0.1% polyoxyethylene (40) stearate: the preparation method was roughly the same as that of tablets comprising 0.5% polyoxyethylene (40) stearate in Example 5. The only difference was that each tablet comprised 0.05 wt % or 0.1 wt % polyoxyethylene (40) stearate, respectively.

Figure 6:
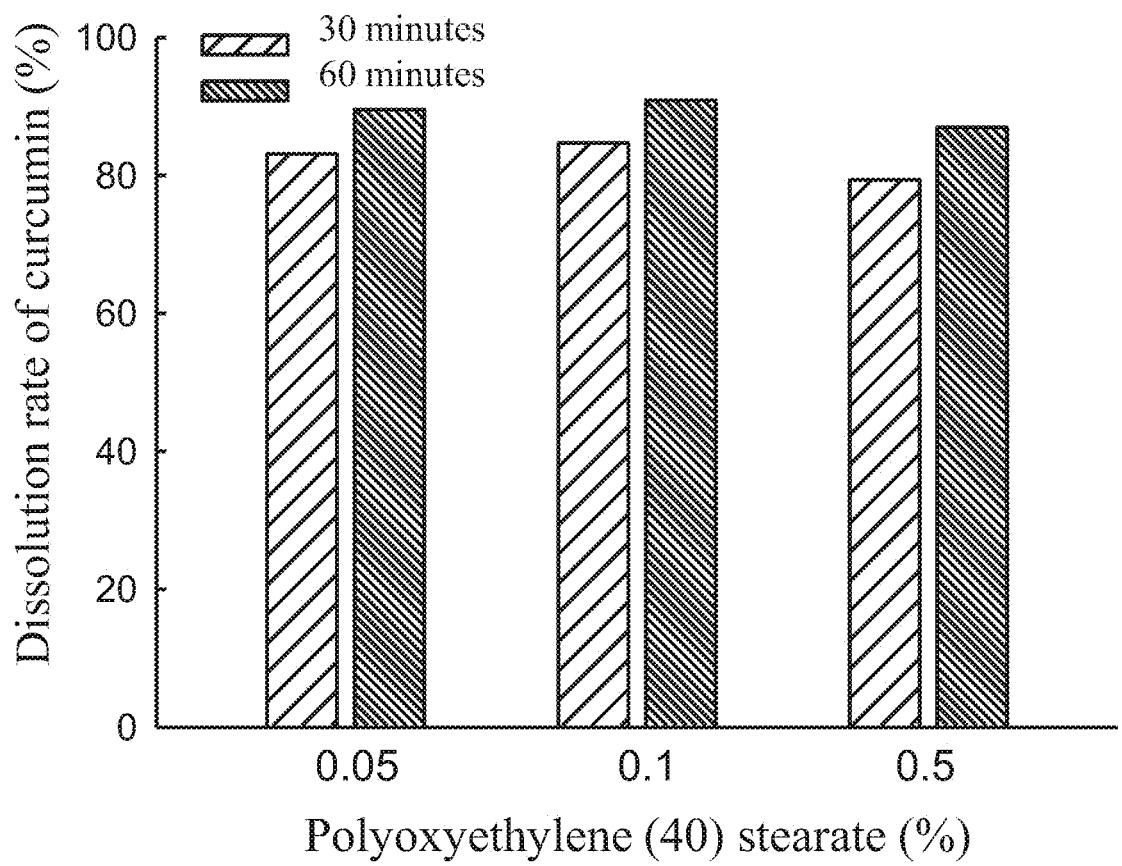
FIG. 6 is a bar graph showing the effect of different concentrations of polyoxyethylene (40) stearate on the dissolution rate of curcumin in the composition of the present invention tested by dissolution testing.

The testing results are shown in FIG. 6. The dissolution rate of curcumin from the tablets comprising 0.05% polyoxyethylene (40) stearate, the tablets comprising 0.1% polyoxyethylene (40) stearate, and the tablets comprising 0.5% polyoxyethylene (40) stearate at 30 minutes was respectively 83.13%, 84.71%, and 79.36%.

Please continue to refer to FIG. 6. The dissolution rate of curcumin from the tablets comprising 0.05% polyoxyethylene (40) stearate, the tablets comprising 0.1% polyoxyethylene (40) stearate, and the tablets comprising 0.5% polyoxyethylene (40) stearate at 60 minutes was respectively 89.54%, 90.88%, and 86.97%, where all reached 85%. Therefore, 0.05-0.5 wt % polyoxyethylene (40) stearate can make the composition comprising epigallocatechin gallate (EGCG) and curcumin of the present invention meet the criteria for oral dosage forms, promote the bioavailability, and at low concentrations can improve the dissolution rate of curcumin.

Example 6-2. The Effect of Different Concentrations of Polysorbate 80 Mixture on the Dissolution Rate of Curcumin Preparing tablets comprising 5% polysorbate 80 mixture: the preparation method was the same as that of tablets comprising 5% polysorbate 80 mixture in Example 5.

Preparing tablets comprising 3% polysorbate 80 mixture, or tablets comprising 10% polysorbate 80 mixture: the preparation method was roughly the same as that of tablets comprising 5% polysorbate 80 mixture in Example 5. The only difference was that each tablet comprised 3 wt % or 10 wt % of polysorbate 80 mixture, respectively.

Figure 7:
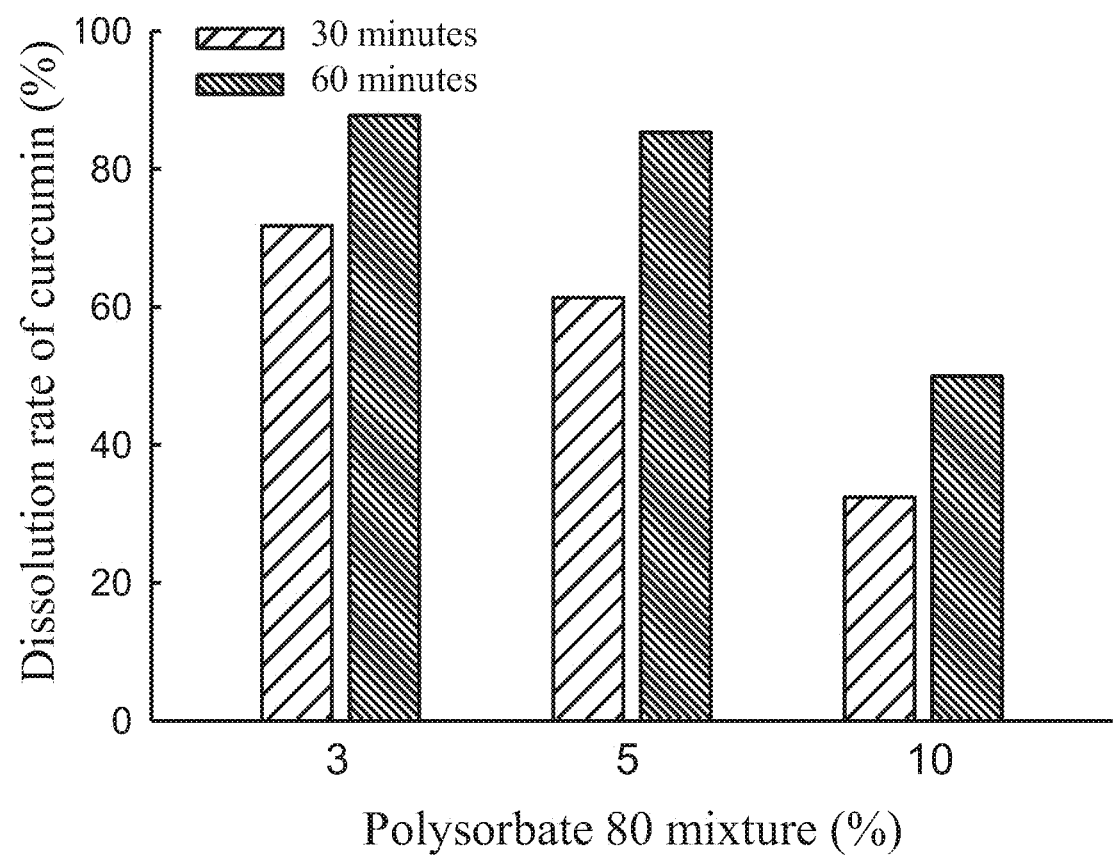
FIG. 7 is a bar graph showing the effect of different concentrations of polysorbate 80 mixture on the dissolution rate of curcumin in the composition of the present invention tested by dissolution testing.

The testing results are shown in FIG. 7. The dissolution rate of curcumin from the tablets comprising 3% polysorbate 80 mixture, the tablets comprising 5% polysorbate 80 mixture, and the tablets comprising 10% polysorbate 80 mixture at 30 minutes was 71.76%, 61.36%, and 32.41%, respectively.

Please continue to refer to FIG. 7. The dissolution rate of curcumin from the tablets comprising 3% polysorbate 80 mixture, the tablets comprising 5% polysorbate 80 mixture, and the tablets comprising 10% polysorbate 80 mixture at 60 minutes was 87.77%, 85.30%, and 49.98%, respectively. Among them, the dissolution rate of curcumin from the tablets comprising 3% polysorbate 80 mixture and the tablets comprising 5% polysorbate 80 mixture at 60 minutes was greater than 85%. Therefore, 3-5 wt % of polysorbate 80 mixture can make the composition comprising epigallocatechin gallate and curcumin of the present invention meet the criteria of oral dosage forms, promote the bioavailability, and at low concentrations can improve the dissolution rate of curcumin.

Example 6-3. The Effect of Different Concentrations of Polyoxyethylene (32) Stearate on the Dissolution Rate of Curcumin Preparing tablets comprising 1% polyoxyethylene (32) stearate: the preparation method was the same as that of tablets comprising 1 wt % polyoxyethylene (32) stearate in Example 5.

Preparing tablets comprising 3% polyoxyethylene (32) stearate, or tablets comprising 5% polyoxyethylene (32) stearate: the preparation method was roughly the same as that of tablets comprising 1% polyoxyethylene (32) stearate in Example 5. The only difference was that each tablet comprised 3 wt % or 5 wt % of polyoxyethylene (32) stearate, respectively.

Figure 8:
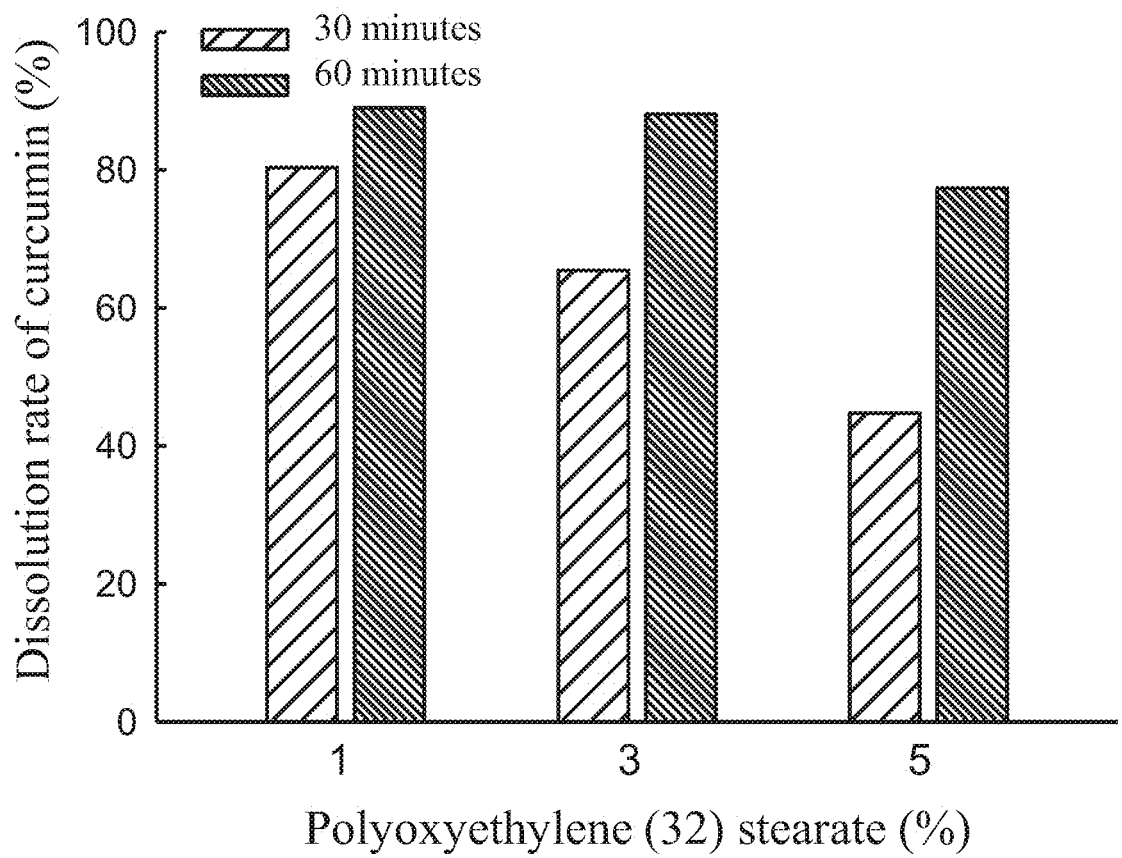
FIG. 8 is a bar graph showing the effect of different concentrations of polyoxyethylene (32) stearate on the dissolution rate of curcumin in the composition of the present invention tested by dissolution testing.

The testing results are shown in FIG. 8. The dissolution rate of curcumin from the tablets comprising 1% polyoxyethylene (32) stearate, the tablets comprising 3% polyoxyethylene (32) stearate, and the tablets comprising 5% polyoxyethylene (32) stearate at 30 minutes was 80.35%, 65.41%, and 44.74%, respectively.

Please continue to refer to FIG. 8. The dissolution rate of curcumin from the tablets comprising 1% polyoxyethylene (32) stearate, the tablets comprising 3% polyoxyethylene (32) stearate, and the tablets comprising 5% polyoxyethylene (32) stearate at 60 minutes was 89.01%, 88.11%, and 77.34%, respectively. Among them, the dissolution rate of curcumin from the tablets comprising 1% polyoxyethylene (32) stearate and the tablets comprising 3% polyoxyethylene (32) stearate at 60 minutes was greater than 85%. Therefore, 1-3 wt % of polyoxyethylene (32) stearate can make the composition comprising epigallocatechin gallate and curcumin of the present invention meet the criteria of oral dosage forms, promote the bioavailability, and at low concentrations can improve the dissolution rate of curcumin.

Example 7. Dissolution Testing III (the Effect of the Ratio of Drugs to Excipients on the Dissolution Rate of Curcumin)

Example 7-1. The Effect of the Ratio of Drugs to Polyoxyethylene (40) Stearate on the Dissolution Rate of Curcumin Preparing tablets with a curcumin to polyoxyethylene (40) stearate weight ratio of 53.3:1: the preparation method was the same as that of tablet comprising 0.5% polyoxyethylene (40) stearate in Example 5. The tablet comprising 0.5% polyoxyethylene (40) stearate in Example 5 comprised 200 mg of turmeric extract, and the turmeric extract used in the present invention comprised at least 80% curcumin. Therefore, the tablet comprising 0.5% polyoxyethylene (40) stearate in Example 5 comprised 160 mg (200 mg×80%=160 mg) of curcumin. Additionally, the total weight of the tablet comprising 0.5% polyoxyethylene (40) stearate in the Example 5 was 600 mg. Therefore, the contained amount of polyoxyethylene (40) stearate was 3 mg (600 mg×0.5%=3 mg). Therefore, the weight ratio of curcumin to polyoxyethylene (40) stearate in the tablet comprising 0.5% polyoxyethylene (40) stearate in the Example 5 was 53.3:1 (160 mg:3 mg=53.3:1)

Preparing tablets with a curcumin to polyoxyethylene (40) stearate weight ratio of 40:1, tablets with a curcumin to polyoxyethylene (40) stearate weight ratio of 48:1, tablets with a curcumin to polyoxyethylene (40) stearate weight ratio of 200:1, tablets with a curcumin to polyoxyethylene (40) stearate weight ratio of 266.7:1, or tablets with a curcumin to polyoxyethylene (40) stearate weight ratio of 533.3:1: the preparation methods were roughly the same as that of tablets comprising 0.5% polyoxyethylene (40) stearate in Example 5. The only difference was that the value of the ratio of the weight of curcumin to polyoxyethylene (40) stearate was respectively 40, 48, 200, 266.7, or 533.3.

Figure 9A:
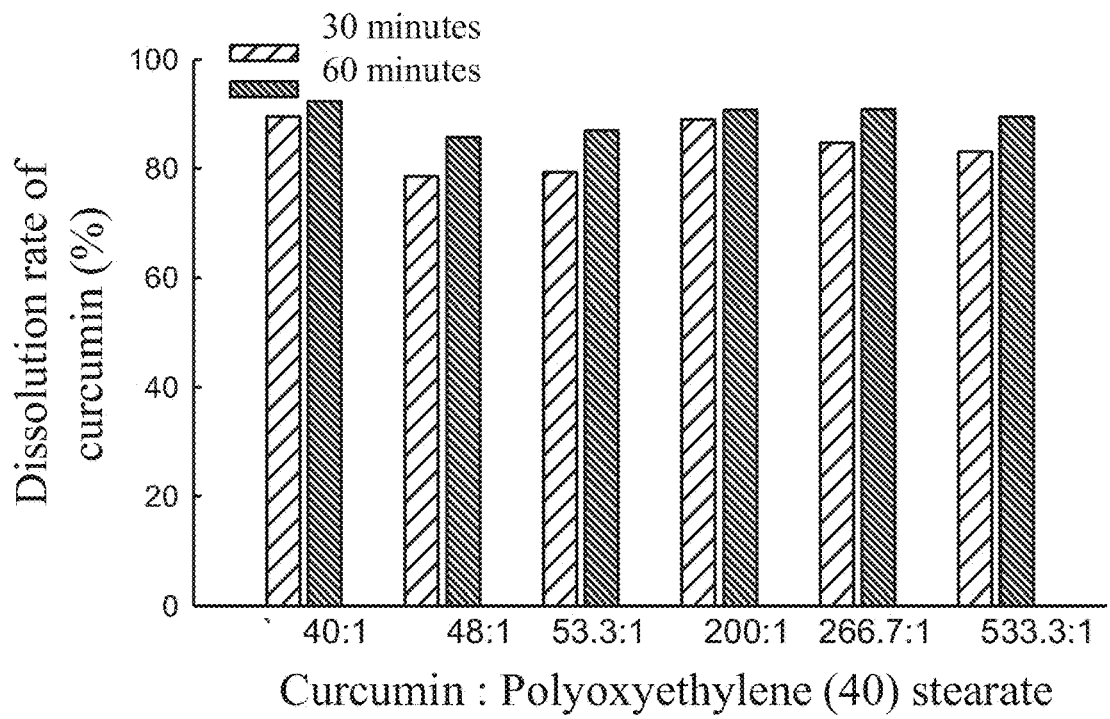
FIG. 9A is a bar graph showing the effect of the ratio of curcumin to polyoxyethylene (40) stearate in the composition of the present invention on the dissolution rate of curcumin tested by dissolution testing.

The testing results are shown in FIG. 9A. The dissolution rates of curcumin from the tablets with the value of the weight ratios of curcumin to polyoxyethylene (40) stearate being 40, 48, 53.3, 200, 266.7, or 533.3 at 30 minutes were respectively 89.57%, 78.56%, 79.36%, 89.00%, 84.71%, and 83.13%.

Please continue to refer to FIG. 9A. The dissolution rates of curcumin from the tablets with the value of the weight ratios of curcumin to polyoxyethylene (40) stearate being 40, 48, 53.3, 200, 266.7, or 533.3 at 60 minutes were respectively 92.40%, 85.75%, 86.97%, 90.72 wt %, 90.88%, and 89.54%, where all was greater than 85%. Therefore, the value of the weight ratios of curcumin to polyoxyethylene (40) stearate being 40, 48, 53.3, 200, 266.7, or 533.3 in the tablets can make the composition comprising epigallocatechin gallate (EGCG) and curcumin of the present invention meet the criteria of oral dosage forms and promote the bioavailability.

Figure 9B:
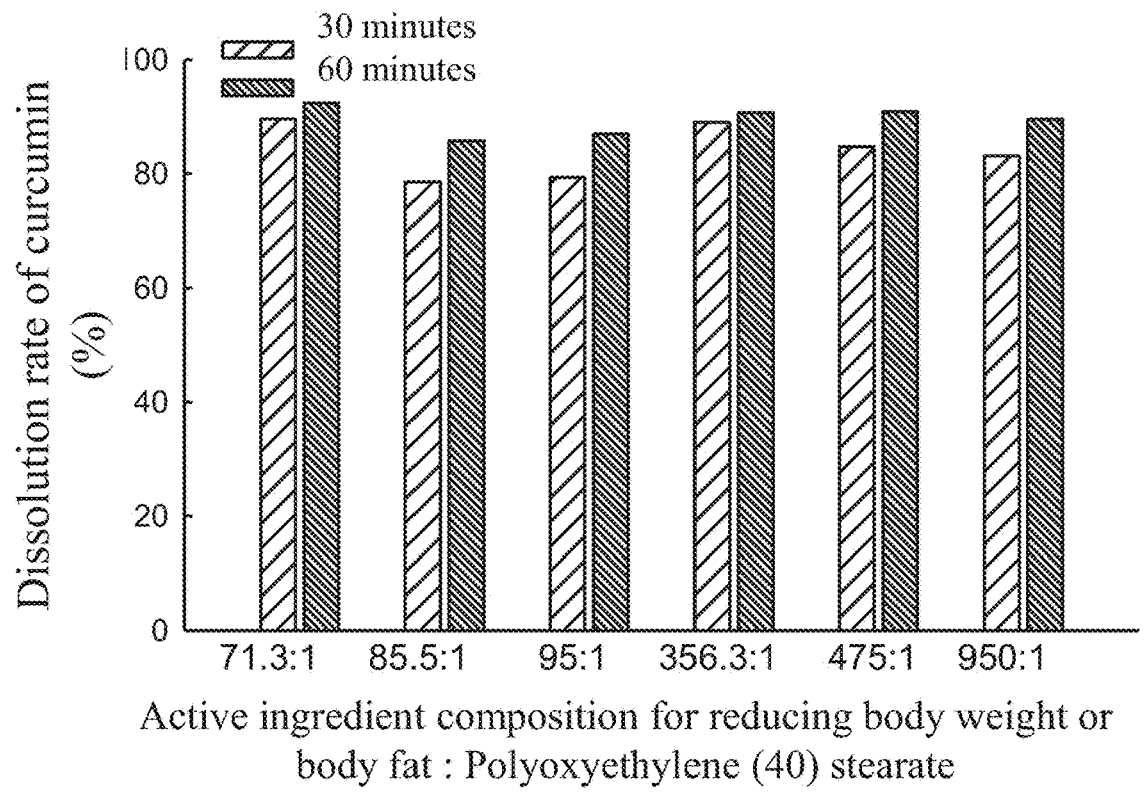
FIG. 9B is a bar graph showing the effect of the ratio of active pharmaceutical ingredient composition for reducing body weight or body fat to polyoxyethylene (40) stearate in the composition of the present invention on the dissolution rate of curcumin tested by dissolution testing.

Please refer to FIG. 9B for the same experimental results. In FIG. 9B, "weight ratio of curcumin to polyoxyethylene (40) stearate" in FIG. 9A was converted to "weight ratio of the active ingredient composition for reducing body weight or body fat to polyoxyethylene (40) stearate." Furthermore, in this Example 7, the active ingredient composition for reducing body weight or body fat is a collective term for the epigallocatechin gallate in green tea extract and the curcumin in turmeric extract.

For example, when the weight ratio of curcumin to polyoxyethylene (40) stearate was 53.3:1 (that is, the aforementioned tablets with the curcumin to polyoxyethylene (40) stearate weight ratio of 53:3.1, and the preparation method was the same as that of tablets comprising 0.5% polyoxyethylene (40) stearate in Example 5), the tablet comprising 0.5% polyoxyethylene (40) stearate in Example 5 comprised 160 mg of curcumin and 3 mg of polyoxyethylene (40) stearate. Furthermore, the tablet comprising 0.5% polyoxyethylene (40) stearate in Example 5 comprised 250 mg of green tea extract, and the green tea extract used in the present invention comprised at least 50% epigallocatechin gallate. Therefore, the tablet comprising 0.5% polyoxyethylene (40) stearate in Example 5 comprised 125 mg (250 mg×50%=125 mg) of epigallocatechin gallate. Therefore, the weight ratio of the active ingredient composition for reducing body weight or body fat to polyoxyethylene (40) stearate in the tablet comprising 0.5% polyoxyethylene (40) stearate was 95:1 [(160 mg+125 mg): 3 mg=95:1].

The testing results are shown in FIG. 9B. When the value of the weight ratio of the active ingredient composition for reducing body weight or body fat to polyoxyethylene (40) stearate in tablets comprising polyoxyethylene (40) stearate was 71.3, 85.5, 95, 356.3, 475, and 950, the dissolution rate of curcumin from the tablets at 30 minutes was respectively 89.57%, 78.56%, 79.36%, 89.00%, 84.71%, and 83.13%.

Please continue to refer to FIG. 9B. When the value of the weight ratio of the active ingredient composition for reducing body weight or body fat to polyoxyethylene (40) stearate in tablets comprising polyoxyethylene (40) stearate was 71.3, 85.5, 95, 356.3, 475, and 950, the dissolution rate of curcumin from the tablets at 60 minutes was respectively 92.40%, 85.75%, 86.97%, 90.72%, 90.88%, and 89.54%, where all was greater than 85%. Therefore, the value of the weight ratio of the active ingredient composition for reducing body weight or body fat to polyoxyethylene (40) stearate of 71.3, 85.5, 95, 356.3, 475, or 950 in the tablet can make the composition comprising epigallocatechin gallate and curcumin of the present invention meet the criteria of oral dosage forms and promote the bioavailability.

Example 7-2. The Effect of the Ratio of Drugs to Polysorbate 80 Mixture on the Dissolution Rate of Curcumin Preparing tablets with a curcumin to polysorbate 80 weight ratio of 5.3:1: the preparation method was the same as that of tablets comprising 5% polysorbate 80 mixture in Example 5. The tablet comprising 5% polysorbate 80 mixture in Example 5 comprised 200 mg of turmeric extract, and the turmeric extract used in the present invention comprised at least 80% curcumin. Therefore, the tablet comprising 5% polysorbate 80 mixture in Example 5 comprised 160 mg (200 mg×80%=160 mg) of curcumin. Additionally, the total weight of the tablet comprising 5% polysorbate 80 mixture in Example 5 was 600 mg. Therefore, the amount of polysorbate 80 mixture in the tablet was 30 mg (600 mg×5%=30 mg). Therefore, the weight ratio of curcumin to polysorbate 80 mixture in the tablet comprising 5% polysorbate 80 mixture in Example 5 was 5.3:1 (160 mg:30 mg=5.3:1)

Preparing tablets with a curcumin to polysorbate 80 mixture weight ratio of 2:1, tablets with a curcumin to polysorbate 80 mixture weight ratio of 6.7:1, tablets with a curcumin to polysorbate 80 mixture weight ratio of 8:1, or tablets with a curcumin to polysorbate 80 mixture weight ratio of 8.9:1: the preparation method was roughly the same as that of tablets comprising 5% polysorbate 80 mixture in Example 5. The only difference was that the value of the weight ratio of curcumin to polysorbate 80 mixture was respectively 2, 6.7, 8, or 8.9.

Figure 10A:
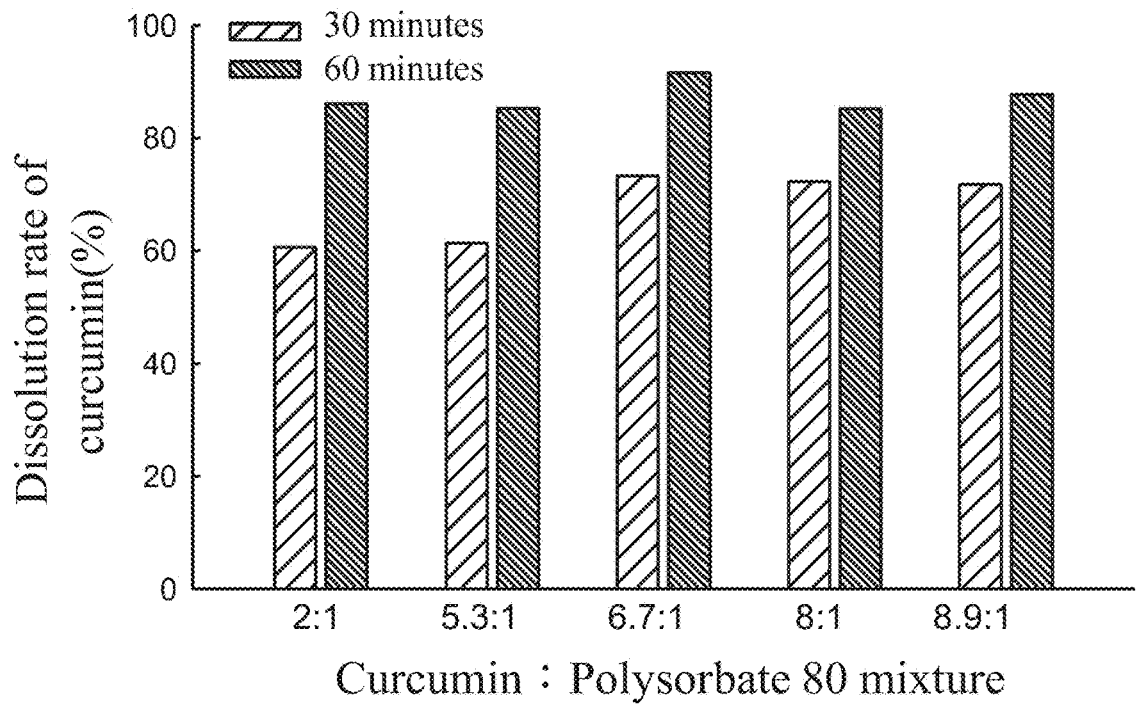
FIG. 10A is a bar graph showing the effect of the ratio of curcumin to polysorbate 80 mixture in the composition of the present invention on the dissolution rate of curcumin tested by dissolution testing.

The testing results are shown in FIG. 10A. When the value of the weight ratio of curcumin to polysorbate 80 mixture in the tablet comprising polysorbate 80 mixture was 2, 5.3, 6.7, 8, and 8.9, the dissolution rate of curcumin from the tablets at 30 minutes was respectively 60.64%, 61.36%, 73.31%, 72.30%, and 71.76%.

Please continue to refer to FIG. 10A. When the value of the weight ratio of curcumin to polysorbate 80 mixture in the tablet comprising polysorbate 80 mixture was 2, 5.3, 6.7, 8, and 8.9, the dissolution rate of curcumin from the tablets at 60 minutes was respectively 86.16%, 85.30%, 91.66%, 85.25%, and 87.77%, where all was greater than 85%. Therefore, the value of the weight ratio of curcumin to polysorbate 80 mixture being 2, 5.3, 6.7, 8, or 8.9 in the tablet can make the composition comprising epigallocatechin gallate (EGCG) and curcumin of the present invention meet the criteria of oral dosage forms and promote the bioavailability.

Figure 10B:
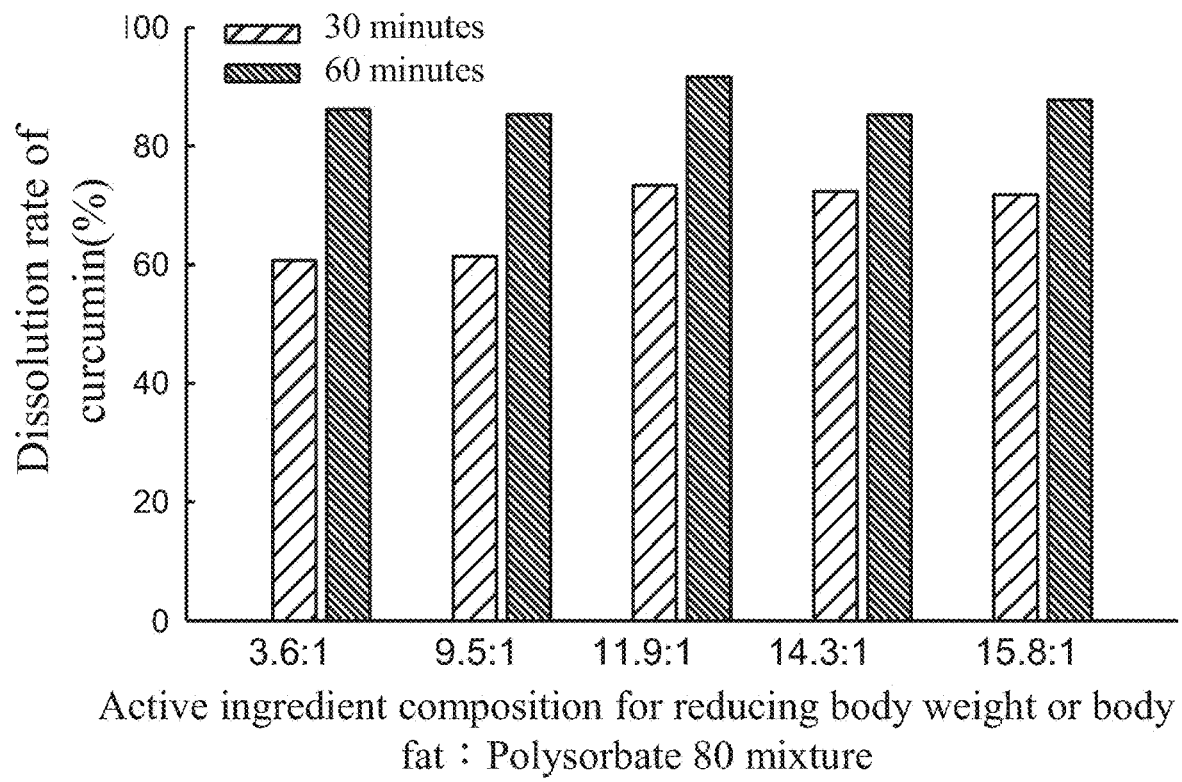
FIG. 10B is a bar graph showing the effect of the ratio of active pharmaceutical ingredient composition for reducing body weight or body fat to polysorbate 80 mixture in the composition of the present invention on the dissolution rate of curcumin tested by dissolution testing.

Please refer to FIG. 10B for the same experimental results. In FIG. 10B, "weight ratio of curcumin to polysorbate 80 mixture" in FIG. 9A was converted to "weight ratio of the active ingredient composition for reducing body weight or body fat to polysorbate 80 mixture." Furthermore, in this Example 7, the active ingredient composition for reducing body weight or body fat is a collective term for the epigallocatechin gallate in green tea extract and the curcumin in turmeric extract.

For example, when the weight ratio of curcumin to polysorbate 80 mixture was 5.3:1 (that is, the aforementioned tablets with the curcumin to polysorbate 80 mixture weight ratio of 5.3:1, and the preparation method was the same as that of tablets comprising 5% polysorbate 80 mixture in Example 5), the tablets comprising 5% polysorbate 80 mixture in Example 5 comprised 160 mg of curcumin and 30 mg of polysorbate 80 mixture. Furthermore, the tablets comprising 5% polysorbate 80 mixture in Example 5 comprised 250 mg of green tea extract, and the green tea extract used in the present invention comprised at least 50% of epigallocatechin gallate. Therefore, the tablet comprising 5% polysorbate 80 mixture in Example 5 comprised 125 mg (250 mg×50 wt %=125 mg) of epigallocatechin gallate. Therefore, the weight ratio of active ingredient composition for reducing body weight or body fat to polysorbate 80 mixture in the tablet comprising 5% polysorbate 80 mixture in the Example 5 was 9.5:1 [(160 mg+125 mg) 30 mg=9.5:1].

The testing results are shown in FIG. 10B. When the value of the weight ratio of the active ingredient composition for reducing body weight or body fat to polysorbate 80 mixture in the tablet comprising polysorbate 80 mixture was 3.6, 9.5, 11.9, 14.3, and 15.8, the dissolution rate of curcumin from the tablets at 30 minutes was respectively 60.64%, 61.36%, 73.31%, 72.30%, and 71.76%.

Please continue to refer to FIG. 10B. When the value of the weight ratio of the active ingredient composition for reducing body weight or body fat to polysorbate 80 mixture in the tablet comprising polysorbate 80 mixture was 3.6, 9.5, 11.9, 14.3, and 15.8, the dissolution rate of curcumin from the tablets at 60 minutes was respectively 86.16%, 85.30%, 91.66%, 85.25%, and 87.77%, where all was greater than 85%. Therefore, the value of the weight ratio of the active ingredient composition for reducing body weight or body fat to polysorbate 80 mixture being 3.6, 9.5, 11.9, 14.3, and 15.8 in the tablet can make the composition comprising epigallocatechin gallate and curcumin of the present invention meet the criteria of oral dosage forms and promote the bioavailability.

Example 7-3. The Effect of the Ratio of Drugs to Polyoxyethylene (32) Stearate on the Dissolution Rate of Curcumin Preparing tablets with a curcumin to polyoxyethylene (32) stearate weight ratio of 5.3:1, tablets with a curcumin to polyoxyethylene (32) stearate weight ratio of 8.9:1, and tablets with a curcumin to polyoxyethylene (32) stearate weight ratio of 26.7:1: the preparation method was roughly the same as that of the tablet comprising 1% polyoxyethylene (32) stearate in Example 5. The only difference was that the weight ratio of curcumin to polyoxyethylene (32) stearate was 5.3, 8.9, or 26.7, respectively.

Figure 11A:
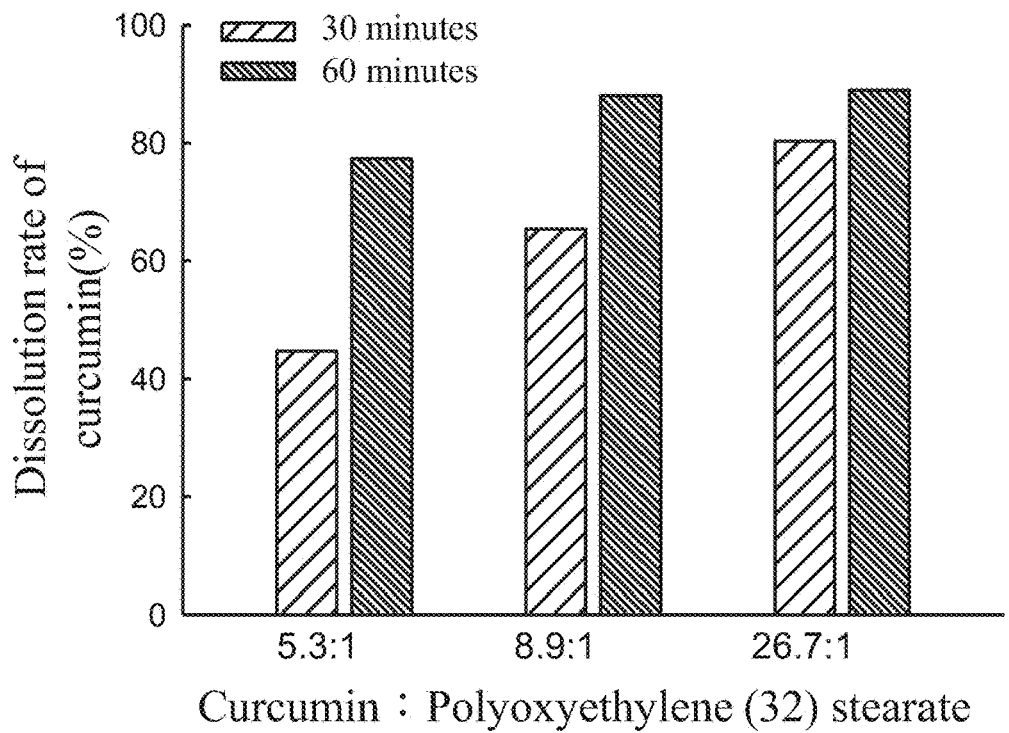
FIG. 11A is a bar graph showing the effect of the ratio of curcumin to polyoxyethylene (32) stearate in the composition of the present invention on the dissolution rate of curcumin tested by dissolution testing.

The testing results are shown in FIG. 11A. When the value of the weight ratio of curcumin to polyoxyethylene (32) stearate in the tablet comprising polyoxyethylene (32) stearate was 5.3, 8.9, or 26.7, the dissolution rate of curcumin from the tablet at 30 minutes was respectively 44.74%, 65.41%, and 80.35%.

Please continue to refer to FIG. 11A. When the value of the weight ratio of curcumin to polyoxyethylene (32) stearate in the tablet comprising polyoxyethylene (32) stearate was 5.3, 8.9, or 26.7, the dissolution rate of curcumin from the tablet at 60 minutes was respectively 77.34%, 88.11%, and 89.01%. Among them, the dissolution rate was greater than 85% when the value of the weight ratio of curcumin to polyoxyethylene (32) stearate was 8.9 or 26.7. Therefore, the value of the weight ratio of curcumin to polyoxyethylene (32) stearate being 8.9 or 26.7 in the tablet can make the composition comprising epigallocatechin gallate and curcumin of the present invention meet the criteria of oral dosage forms and promote the bioavailability.

Figure 11B:
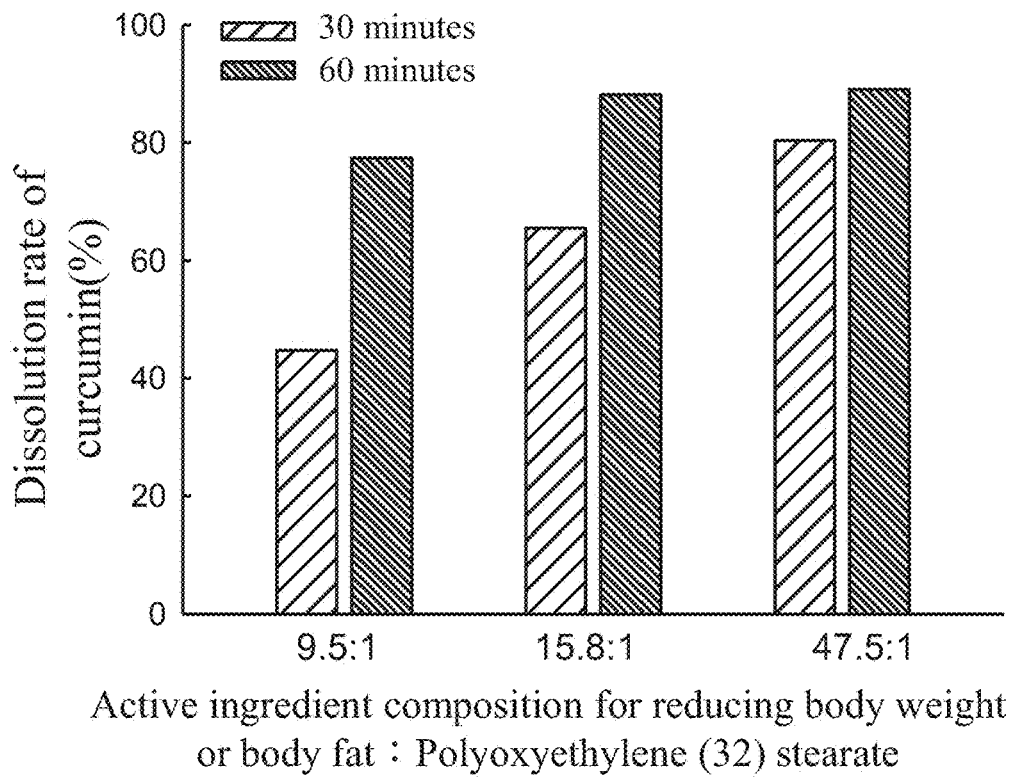
FIG. 11B is a bar graph showing the effect of the ratio of active pharmaceutical ingredient composition for reducing body weight or body fat to polyoxyethylene (32) stearate in the composition of the present invention on the dissolution rate of curcumin tested by dissolution testing.

Please refer to FIG. 11B for the same experimental results. In FIG. 11B, "weight ratio of curcumin to polyoxyethylene (32) stearate" in FIG. 11A was converted to "weight ratio of the active ingredient composition for reducing body weight or body fat to polyoxyethylene (32) stearate."

The testing results are shown in FIG. 11B. When the value of the weight ratio of the active ingredient composition for reducing body weight or body fat to polyoxyethylene (32) stearate in the tablet comprising polyoxyethylene (32) stearate was 9.5, 15.8, or 47.5, the dissolution rate of curcumin from the tablet at 30 minutes was respectively 44.74%, 65.41%, and 80.35%.

Please continue to refer to FIG. 11B. When the value of the weight ratio of the active ingredient composition for reducing body weight or body fat to polyoxyethylene (32) stearate in the tablet comprising polyoxyethylene (32) stearate was 9.5, 15.8, or 47.5, the dissolution rate of curcumin from the tablet at 60 minutes was respectively 77.34%, 88.11%, and 89.01%. Among them, the dissolution rate was greater than 85% when the value of the weight ratio of the active ingredient composition for reducing body weight or body fat to polyoxyethylene (32) stearate was 15.8 or 47.5. Therefore, the value of the weight ratio of the active ingredient composition for reducing body weight or body fat to polyoxyethylene (32) stearate being 15.8 or 47.5 in the tablet can make the composition comprising epigallocatechin gallate and curcumin of the present invention meet the criteria of oral dosage forms and promote the bioavailability.

Example 8. Animal Experiment II (Drug Administration During Obesity Induction)

The test substances of this experiment were prepared as follows:

Preparing an ME00R5 composition: Mixing ME00C1A and an appropriate amount of sterile water to a total concentration of 108.5 mg/mL (milligrams solute per milliliter of solution) of green tea extract and turmeric extract to obtain the ME00R5 composition Wherein, based on the total weight of ME00C1A, the green tea extract was 55.5 wt %, and the turmeric extract was 44.5 wt %.

Preparing an ME00R composition: Mixing ME00C1A, piperine, and an appropriate amount of sterile water to a total concentration of 108.5 mg/mL of green tea extract and turmeric extract to obtain the ME00R composition. Wherein, the content of green tea extract and the content of turmeric extract were identical as those of the ME00R5 composition. Based on the total weight of the ME00R composition, the piperine was 0.1-0.5 wt %. Based on the total volume of the ME00R composition, the concentration of piperine was 0.525-2.625 mg/mL (milligrams solute per milliliter of solution.)

Preparing an ME00C1B composition: Mixing ME00C1A, piperine, glyceryl dibehenate, and an appropriate amount of sterile water to a total concentration of 108.5 mg/mL of green tea extract and turmeric extract to obtain the ME00C1B composition. Wherein, the content of green tea extract and the content of turmeric extract were identical as those of the ME00R5 composition. Based on the total weight of the ME00C1B composition, the piperine was 0.1-0.5 wt %, and the glyceryl dibehenate was 0.5-1.2 wt %. Based on the total volume of the ME00C1B composition, the concentration of piperine was 0.525-2.625 mg/mL, and the concentration of glyceryl dibehenate was 2.625-6.3 mg/mL (milligrams solute per milliliter of solution.)

Preparing an ME00C2B composition: Mixing ME00C1A, piperine, polyoxyethylene (32) stearate, and an appropriate amount of sterile water to a total concentration of 108.5 mg/mL of green tea extract and turmeric extract to obtain the ME00C2B composition. Wherein, the content of green tea extract and the content of turmeric extract were identical as those of the ME00R5 composition. Based on the total weight of the ME00C2B composition, the piperine was 0.1-0.5 wt %, and the polyoxyethylene (32) stearate was 0.5-1.2 wt %. Based on the total volume of the ME00C2B composition, the concentration of piperine was 0.525-2.625 mg/mL, and the concentration of polyoxyethylene (32) stearate was 2.625-6.3 mg/mL (milligrams solute per milliliter of solution.)

Preparing an ME00C3B composition: Mixing ME00C1A, piperine, polysorbate 80 mixture, and an appropriate amount of sterile water to a total concentration of 108.5 mg/mL of green tea extract and turmeric extract to obtain the ME00C3B composition. Wherein, the content of green tea extract and the content of turmeric extract were identical as those of the ME00R5 composition. Based on the total weight of the ME00C3B composition, the piperine was 0.1-0.5 wt %, and the polysorbate 80 mixture was 0.5-1.2 wt %. Based on the total volume of the ME00C3B composition, the concentration of piperine was 0.525-2.625 mg/mL, the concentration of polysorbate 80 mixture was 2.625-6.3 mg/mL (milligrams solute per milliliter of solution.) Wherein, the polysorbate 80 mixture was a mixture comprising polysorbate 80 and magnesium aluminometasilicate.

The concentration of piperine in said ME00R composition, ME00C1B composition, ME00C2B composition, and ME00C3B composition was identical.

The weight percentage of glyceryl dibehenate in said ME00C1B composition was identical to that of polyoxyethylene (32) stearate in said ME00C2B composition.

In this experimental example, 7-week old male SD rats were used and divided into a obesity control group (that is, the HFD group), an ME00R composition of the present invention group, an ME005R group, an ME00C1B group, an ME00C2B group, and an ME00C3B group. Each group included 4 rats for experimentation. The rats were fed with high-fat diet for 8 consecutive weeks to induce obesity, and during the same period were daily fed by oral gavage a test substance (the dosing volume of the test substance each time was 3 mL per kg of body weight of the rat; the daily dosage of the test substance was 325.5 mg per kg of body weight of the rat per day). Rats in the obesity control group were fed equal volumes of sterile water to evaluate the difference in body weight and visceral fat of rats in each group. During the experiment, the body weight and the average food intake of each rat were recorded weekly. The rats were fasted for 8-12 hours in the evening prior to experiment completion. Then, the rats were sacrificed to weigh their empty body weight, and their epididymal fat, perirenal fat, and mesenteric fat were dissected and weighed to calculate the amount of visceral fat. The relative body fat percentage (%) was calculated as follows:

The weight of visceral fat÷the empty body weight=body fat percentage

The body fat percentage÷average of body fat percentage of rats in the obesity control group× 100%=relative body fat percentage The data of each group are expressed as mean±SD. Letters a, b, and c indicate the results of statistical analysis, wherein different letters indicate significant statistical difference between groups (p<0.05), and identical letters indicate no significant statistical difference between groups (p>0.05).

Figure 12A:
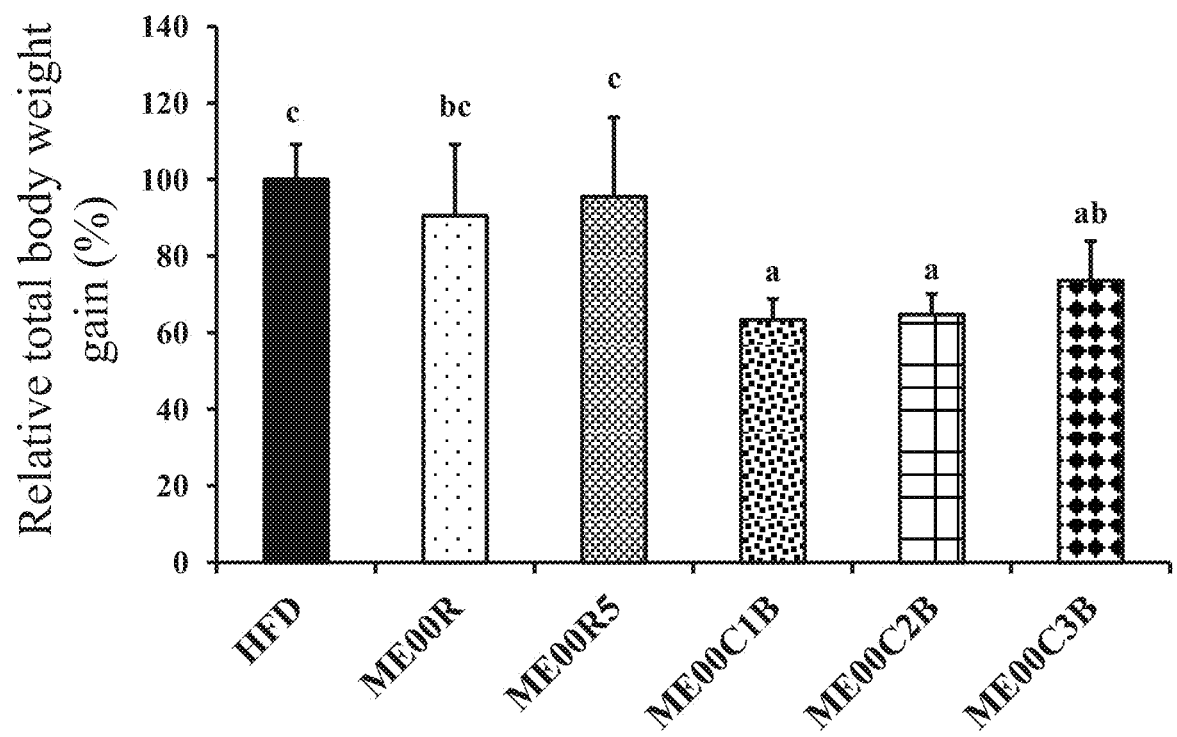
FIG. 12A is a bar graph showing the effect of compositions comprising each of the three different excipients on the total body weight gain of each group of rats tested by administering drugs during obesity induction.

The experimental results are shown in FIG. 12A. Comparing to the ME00R5 group, rats administered with ME00C1B, ME00C2B, or ME00C3B showed significantly reduced body weight gain (p<0.05). Therefore, glyceryl dibehenate and piperine can significantly promote the weight loss efficacy of the composition of the present invention; polyoxyethylene (32) stearate and piperine can significantly promote the weight loss efficacy of the composition of the present invention; polysorbate 80 mixture and piperine can also significantly promote the weight loss efficacy of the composition of the present invention.

Figure 12B:
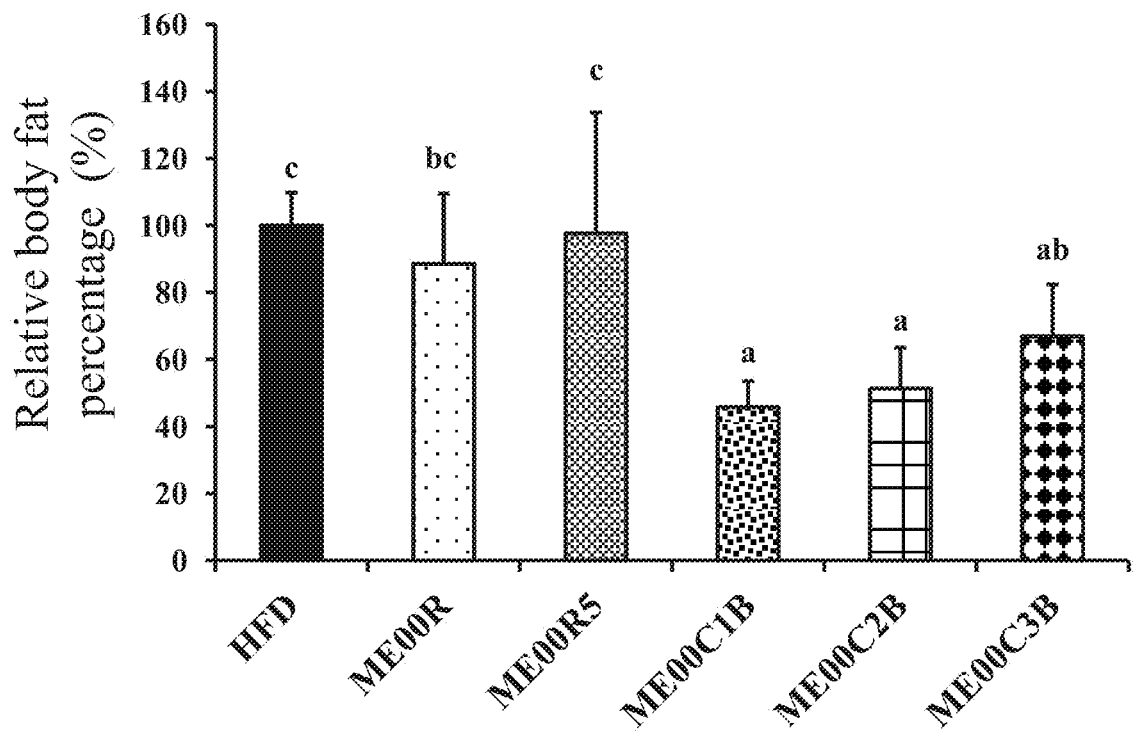
FIG. 12B is a bar graph showing the effect of the composition comprising each of the three different excipients on the body fat percentage of each group of rats tested by administering drugs during obesity induction.

The experimental results shown in FIG. 12B also demonstrate that rats administered with ME00C1B, ME00C2B, or ME00C3B showed significantly decreased body fat percentage (p<0.05) comparing to the ME00R5 group. Therefore, glyceryl dibehenate and piperine can significantly promote the fat loss efficacy of the composition of the present invention; polyoxyethylene (32) stearate and piperine can significantly promote the fat loss efficacy of the composition of the present invention; polysorbate 80 mixture and piperine can also significantly promote the fat loss efficacy of the composition of the present invention.

These experiments demonstrate that excipients can significantly promote the weight loss efficacy and the fat loss efficacy of the composition of the present invention, and increase the bioavailability of the composition of the present invention.

Example 9. Animal Experiment III (Drug Administration During Obesity Induction)

The test substances of this experiment were prepared as follows:

Preparing an ME00C1B composition: the preparation method was the same as that of the ME00C1B composition in the Example 8. The ratio of turmeric extract to green tea extract in the ME00C1B composition was 4:5.

Preparing an ME00C14 composition: the preparation method was the same as that of the ME00C1B composition in Example 8. The only difference was that the ratio of turmeric extract to green tea extract in the ME00C14 composition was 2:1.

Preparing an ME00D11 composition: the preparation method was the same as that of the ME00C1B composition in Example 8. The only difference was that the ratio of turmeric extract to green tea extract in the ME00D11 composition was 1:2.

Preparing an ME00D14 composition: the preparation method was the same as that of the ME00C1B composition in Example 8. The only difference was that the ratio of turmeric extract to green tea extract in the ME00D14 composition was 1:5.

In this experimental example, 7-week old male SD rats were used and divided into an obesity control group (that is, the HFD group), an ME00C14 composition group, an ME00D11 group, an ME00D14 group, and an ME00C1B group. Each group included 4 rats for experimentation. The rats were fed with high-fat diet for 8 consecutive weeks to induce obesity, and during the same period were daily fed by oral gavage a test substance (the dosing volume of the test substance was each time 3 mL per kg of body weight of the rat; the daily dosage of the test substance was 325.5 mg per kg of body weight of the rat per day). Rats in the obesity control group were fed equal volumes of sterile water to evaluate the difference in body weight and visceral fat of rats in each group. During the experiment, the body weight and the average food intake of each rat were recorded weekly. The rats were fasted for 8-12 hours in the evening prior to experiment completion. Then, the rats were sacrificed to weigh their empty body weight, and their epididymal fat, perirenal fat, and mesenteric fat were dissected and weighed to calculate the amount of visceral fat. The calculation method was the same as that of Example 8.

Figure 13A:
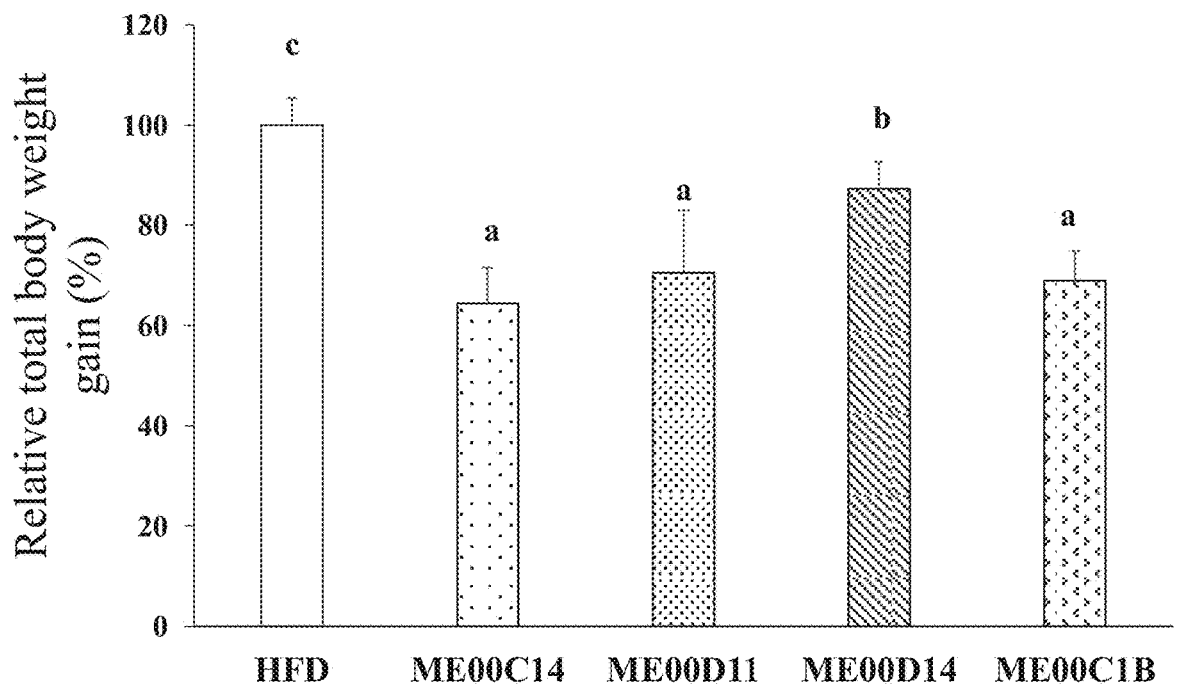
FIG. 13A is a bar graph showing the effect of compositions comprising different ratios of ingredients on the total body weight gain of each group of rats tested by administering drugs during obesity induction.

The experimental results are shown in FIG. 13A. Comparing to the obesity control group, rats administered with ME00C14, ME00D11, ME00D14, and ME00C1B showed significantly reduced body weight gain ($p<0.05$).

Figure 13B:
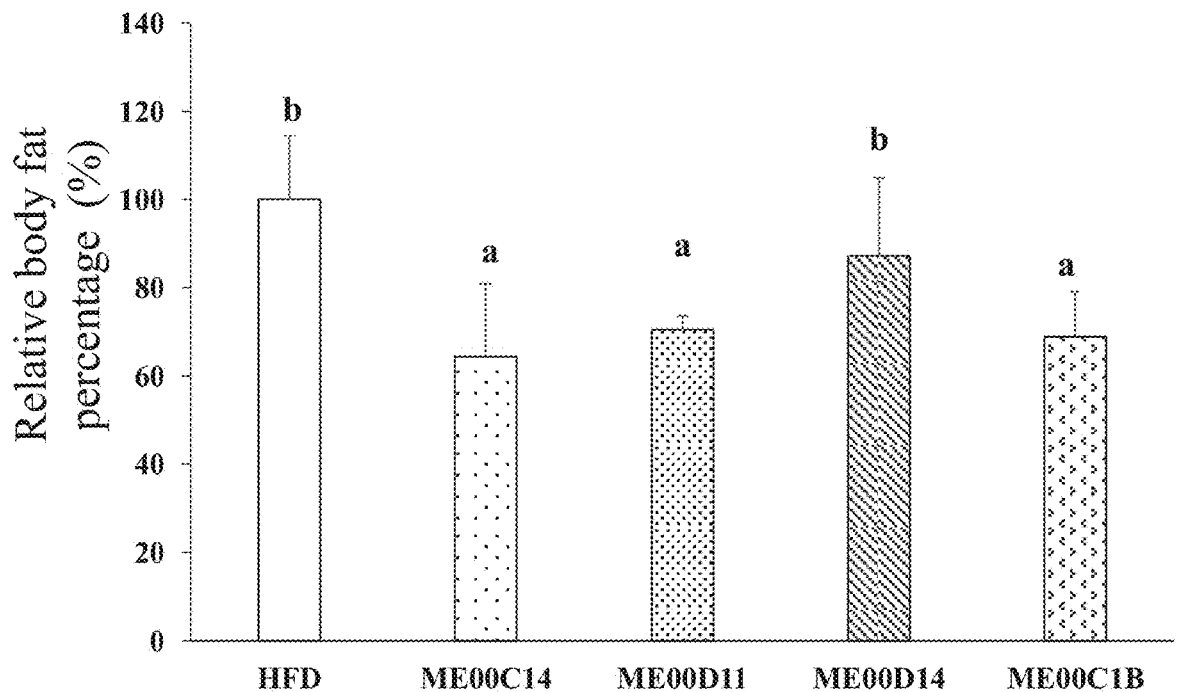
FIG. 13B is a bar graph showing the effect of compositions comprising different ratios of ingredients on the body fat percentage of each group of rats tested by administering drugs during obesity induction.

The experimental results shown in FIG. 13B also demonstrate that comparing to the obesity control group, rats administered with ME00C14, ME00D11, and ME00C1B showed significantly decreased body fat percentage ($p<0.05$).

These experiments demonstrate that specific ratios of green tea extract to turmeric extract can significantly promote the weight loss efficacy and the fat loss efficacy.

Example 10. Animal Experiment IV (Drug Administration after Obesity Induction)

The test substances of this experiment were prepared as follows:

Preparing an ME00C4A composition: mixing 250 mg of green tea extract, 200 mg of turmeric extract, piperine, polyoxyethylene (40) stearate, and an appropriate amount of sterile water to obtain the ME00C4A composition. Wherein, based on the total weight of the ME00C4A composition, the piperine was 0.1-0.5 wt %, and the polyoxyethylene (40) stearate was 0.5-1.2 wt %. Based on the total volume of the ME00C4A composition, the concentration of piperine was 0.525-2.625 mg/mL, and the concentration of polyoxyethylene (40) stearate was 2.625-6.3 mg/mL (milligrams solute per milliliter of solution).

In this experimental example, male SD rats were used and divided into a normal diet control group (that is, the NFD-C group), a high-fat high-cholesterol diet control group (that is, the HFD-C group), and an ME00C4A group. Other than the normal diet control group that was fed with normal diets, rats in the other groups were fed with high-fat high-cholesterol diet for 8 consecutive weeks to induce obesity, fatty liver, and non-alcoholic steatohepatitis (NASH). Rats in the ME00C4A group were daily fed by oral gavage with the ME00C4A composition for eight consecutive weeks (the daily administered dosage was 372 mg per kg of body weight of the rat per day); Rats in the normal diet control group (that is, the NFD-C group) and the high-fat high-cholesterol diet control group (that is, the HFD-C group) were fed with equal volumes of sterile water. During the experiment, the rats in the high-fat high-cholesterol diet control group (that is, the HFD-C group) and the ME00C4A group were continuously fed with high-fat high-cholesterol diet. The body weight and the average food intake of each rat were recorded daily. After the experiment was completed, the rats were fasted for 8-10 hours. Then, the rats were sacrificed to weigh their empty body weight, and their epididymal fat, perirenal fat, and mesenteric fat were dissected and weighed to calculate the amount of visceral fat. The calculation method was the same as that of Example 8. The whole liver of rat was weighed. Part of the liver tissue was homogenized by a homogenizer, and the level of fat, cholesterol, and triglyceride was measured by different ELISA kits. Furthermore, the liver was sectioned and histologically stained to evaluate the level of liver inflammation in the rats based on NAFLD Activity Score (NAS; please refer to Table 2 for scoring criteria). If the NAFLD Activity Score of the rat is greater than or equal to 5, the rat has non-alcoholic steatohepatitis.

Based on the NAFLD Activity Score analysis of the histologically stained tissues, this experiment had successfully induced fatty liver and non-alcoholic steatohepatitis in the rats.

Figure 14A:
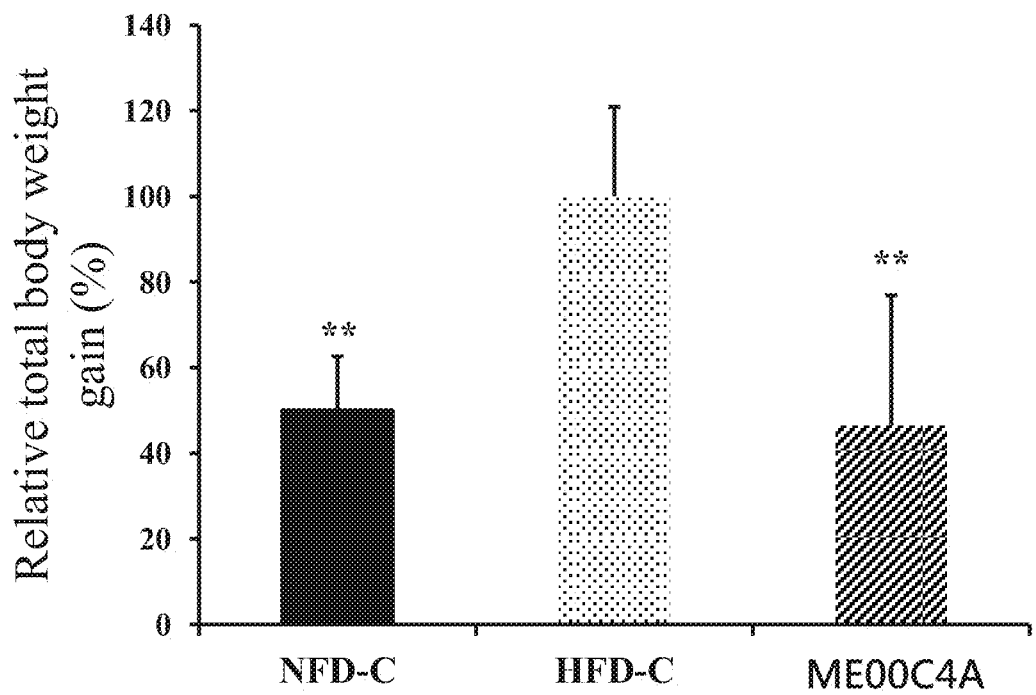
FIG. 14A is a bar graph showing the effect of the compositions of the present invention on the total body weight gain of rats with fatty liver and non-alcoholic steatohepatitis tested by administering drugs after obesity induction.
Figure 14B:
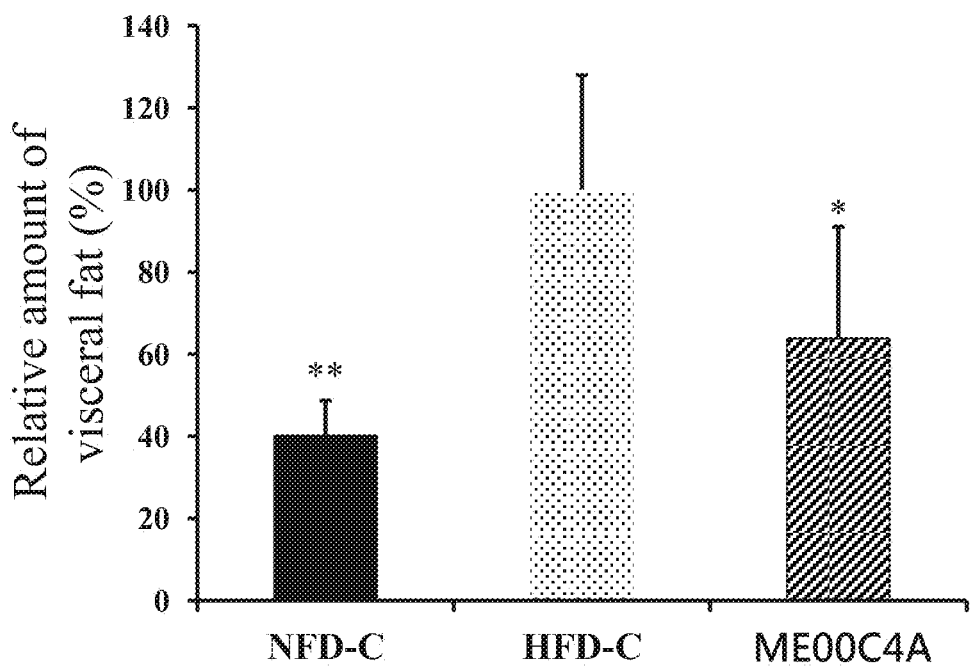
FIG. 14B is a bar graph showing the effect of the compositions of the present invention on the body fat percentage of rats with fatty liver and non-alcoholic steatohepatitis tested by administering drugs after obesity induction.
Figure 15A:
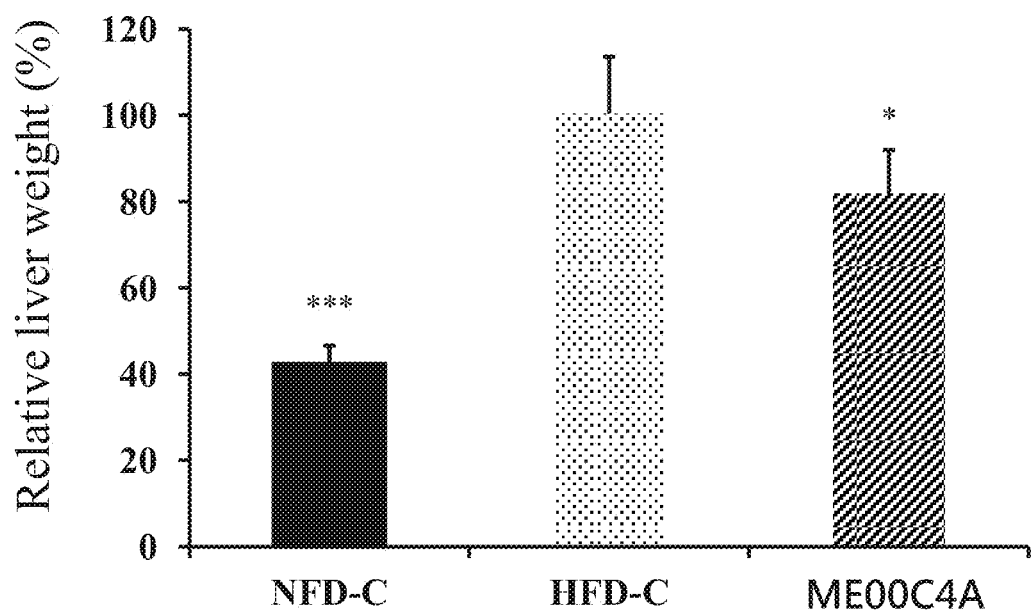
FIG. 15A is a bar graph showing the effect of the compositions of the present invention on the liver weight of rats with fatty liver and non-alcoholic steatohepatitis tested by administering drugs after obesity induction.
Figure 15B:
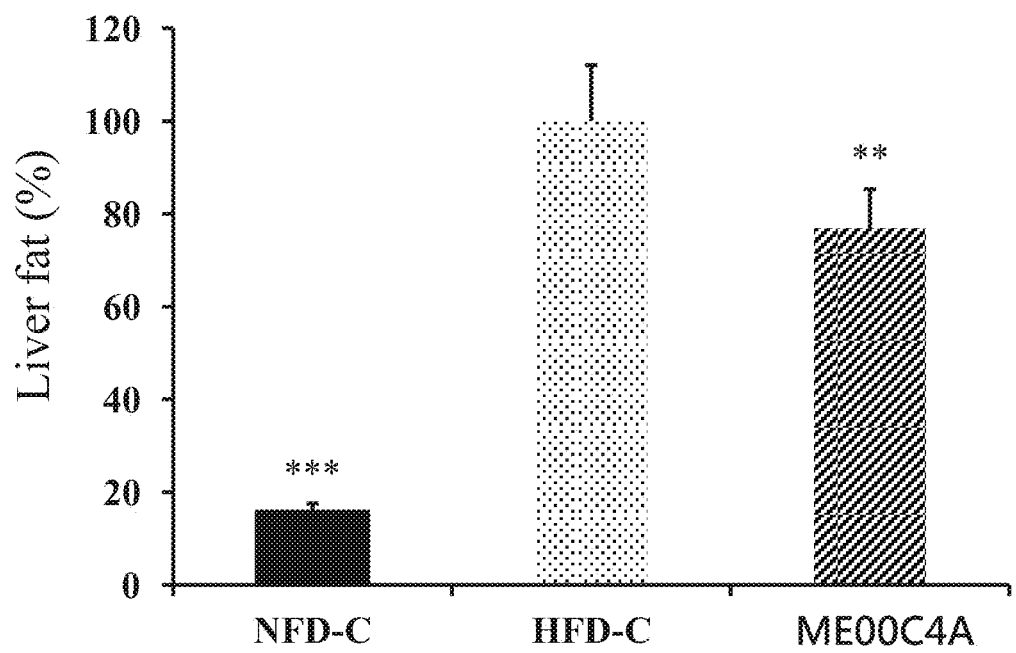
FIG. 15B is a bar graph showing the effect of the compositions of the present invention on the amount of liver fat of rats with fatty liver and non-alcoholic steatohepatitis tested by administering drugs after obesity induction.
Figure 15C:
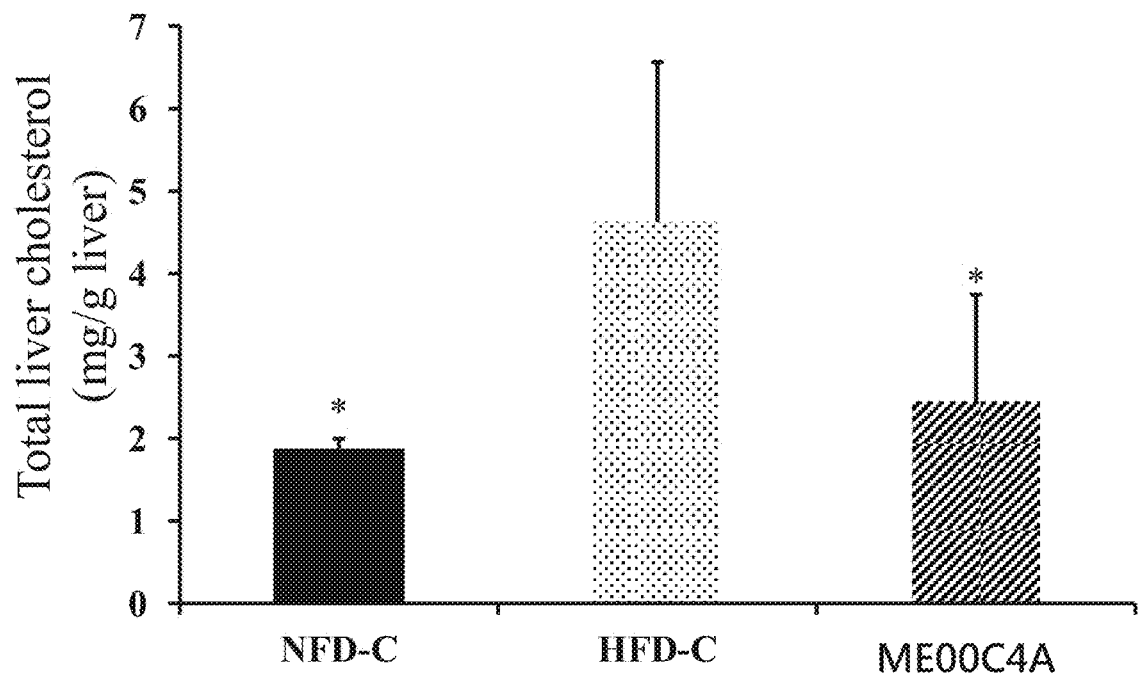
FIG. 15C is a bar graph showing the effect of the compositions of the present invention on the liver total cholesterol of rats with fatty liver and non-alcoholic steatohepatitis tested by administering drugs after obesity induction.
Figure 15D:
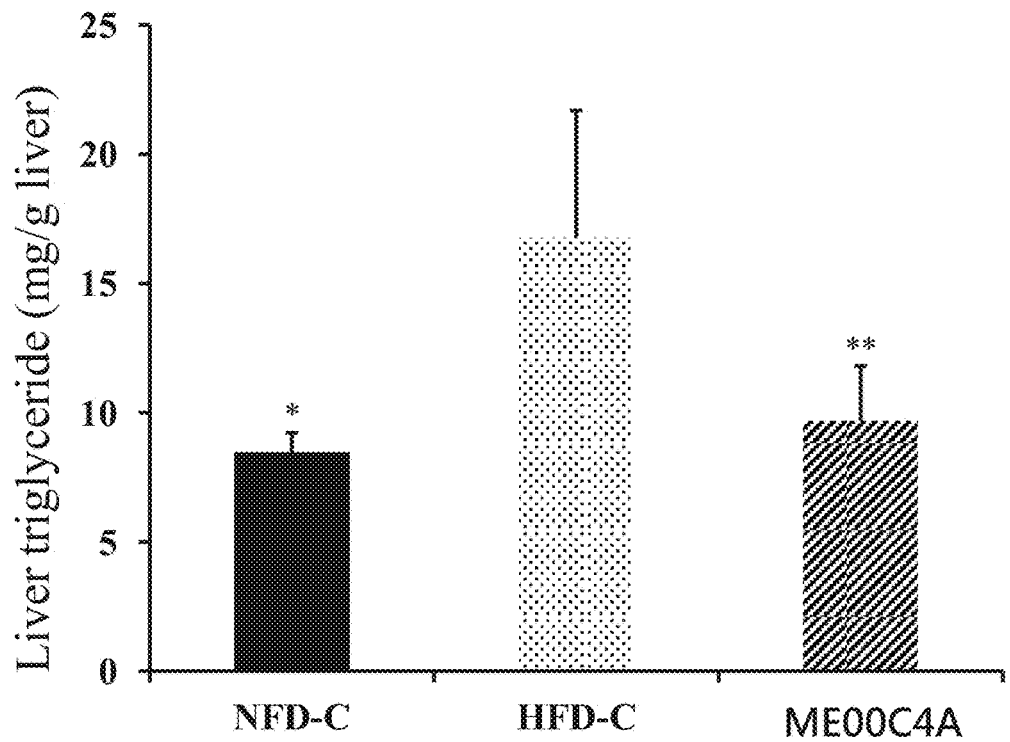
FIG. 15D is a bar graph showing the effect of the compositions of the present invention on the liver triglyceride of rats with fatty liver and non-alcoholic steatohepatitis tested by administering drugs after obesity induction.

Please refer to FIGS. 14A-14B. Comparing to the high-fat high-cholesterol diet control group (that is, the HFD-C group), rats administered with ME00C4A showed significantly reduced relative body weight gain and body fat percentage ($p<0.05$.)

Based on the experimental results, the compositions with excipients of the present invention demonstrate significant weight loss efficacy and fat loss efficacy in rats with fatty liver and non-alcoholic steatohepatitis.

TABLE 2

Scoring criteria of NAFLD Activity Scoring system

| Steatosis grade (0-3) | Lobular inflammation (0-3) | Hepatocyte ballooning (0-2) |
|---|---|---|
| 0: <5% | 0: None | 0: None |
| 1: 5-33% | 1: <2 foci/* 20 field | 1: Mild, few |
| 2: 34-66% | 2: 2-4 foci/* 20 field | 2: Moderate-many |
| 3: >66% | 3: >4 foci/* 20 field | |
| NAFLD activity score (NAS): 0-8 | 0-2 not NASH | |
| | 3-4 uncertain for NASH | |
| | 5-8 NASH | |

Non-Alcoholic Steatohepatitis (NASH) Clinical Research Network Fibrosis Staging System Please refer to FIGS. 15A-15D. Comparing to the high-fat high-cholesterol diet control group (that is, the HFD-C group), rats administered with ME00C4A showed significantly decreased liver weight, level of liver fat, level of total liver cholesterol, and level of liver triglyceride (p<0.05).

Based on these experimental results, the compositions with excipients in the present invention can significantly reduce the liver weight, level of liver fat, level of liver total cholesterol, and level of liver triglyceride in rats with fatty liver and non-alcoholic steatohepatitis, thereby achieving the efficacy of treating fatty liver and non-alcoholic steatohepatitis.

The above descriptions are merely the preferred embodiments, and are not limitations to the present invention in any form; even though the preferred embodiments of the present invention are disclosed above, they are not used to limit the present invention by any means. Any person skilled in the art, without deviation from the scope of the technical plan of the present invention, could use the above disclosed technical information to make equivalently effective embodiments with equivalent changes by several adjustments or modifications, but any simple modification, equivalent change, and modification substantially made to the above embodiments according to the techniques of the present invention, while not deviating from the technical plans of the present invention, should still belong within the scope of the technical plans of the present invention.

What is claimed is:

1. A composition for reducing body weight or body fat, comprising:
   (a) an excipient; and
   (b) an active ingredient composition for reducing body weight or body fat, wherein the active ingredient composition for reducing body weight or body fat comprises epigallocatechin gallate (EGCG) and curcumin; and wherein the excipient is selected from the group consisting of glyceryl dibehenate, polyoxyethylene stearates, a polysorbate 80 mixture, wherein the polysorbate 80 mixture comprises polysorbate 80 and aluminometasilicate, vitamin E polyethylene glycol succinate, oleoyl polyoxyl-6 glycerides, and a combination thereof.

2. The composition for reducing body weight or body fat according to claim 1, further comprising at least one of glyceryl palmitostearate, polysorbate 20, poloxamer, and polyethylene glycols, or a combination thereof.

3. The composition for reducing body weight or body fat according to claim 1, further comprising piperine.

4. The composition for reducing body weight or body fat according to claim 1, wherein, said polyoxyethylene stearate is polyoxyethylene (32) stearate, and the weight percentage of said polyoxyethylene (32) stearate is 0.1-20% based on the total weight of said composition for reducing body weight or body fat; or, the weight percentage of said polysorbate 80 mixture is 0.5-20% based on the total weight of said composition for reducing body weight or body fat; or, said polyoxyethylene stearate is polyoxyethylene (40) stearate, and the weight percentage of said polyoxyethylene (40) stearate is 0.005-6.7% based on the total weight of said composition for reducing body weight or body fat.

5. The composition for reducing body weight or body fat according to claim 1, wherein, said polyoxyethylene stearate is polyoxyethylene (32) stearate, and the weight percentage of said polyoxyethylene (32) stearate is 1-15% based on the total weight of said composition for reducing body weight or body fat; or, the weight percentage of said polysorbate 80 mixture is 1-15% based on the total weight of said composition for reducing body weight or body fat; or, said polyoxyethylene stearate is polyoxyethylene (40) stearate, and the weight percentage of said polyoxyethylene (40) stearate is 0.01-3.3% based on the total weight of said composition for reducing body weight or body fat.

6. The composition for reducing body weight or body fat according to claim 1, wherein said polyoxyethylene stearate is polyoxyethylene (32) stearate, and the weight percentage of said polyoxyethylene (32) stearate is 1-10% based on the total weight of said composition for reducing body weight or body fat; or, the weight percentage of said polysorbate 80 mixture is 3-10% based on the total weight of said composition for reducing body weight or body fat; or, said polyoxyethylene stearate is polyoxyethylene (40) stearate, and the weight percentage of said polyoxyethylene (40) stearate is 0.05-1% based on the total weight of said composition for reducing body weight or body fat.

7. The composition for reducing body weight or body fat according to claim 1, wherein said polyoxyethylene stearate is polyoxyethylene (32) stearate, and the value of the ratio of the weight of said curcumin to the weight of said polyoxyethylene (32) stearate is 5.3-26.7; or, the value of the ratio of the weight of said curcumin to the weight of said polysorbate 80 mixture is 2-8.9; or, said polyoxyethylene stearate is polyoxyethylene (40) stearate, and the value of the ratio of the weight of said curcumin to the weight of said polyoxyethylene (40) stearate is 40-533.3; or, said polyoxyethylene stearate is polyoxyethylene (32) stearate, and the value of the ratio of the weight of said active ingredient composition for reducing body weight or body fat to the weight of said polyoxyethylene (32) stearate is 9.5-47.5; or, the value of the ratio of the weight of said active ingredient composition for reducing body weight or body fat to the weight of said polysorbate 80 mixture is 3.6-15.8; or, said polyoxyethylene stearate is polyoxyethylene (40) stearate, and the value of the ratio of the weight of said active ingredient composition for reducing body weight or body fat to the weight of said polyoxyethylene (40) stearate is 71.3-950.

8. The composition for reducing body weight or body fat according to claim 1, further comprising at least one of mannitol, microcrystalline celluloses, sodium dodecyl sulfate (SDS), and cross-linked sodium carboxymethyl cellulose, croscarmellose sodium or a combination thereof.

9. The composition for reducing body weight or body fat according to claim 1, wherein, the value of the ratio of the weight of said curcumin to the weight of said epigallocatechin gallate (EGCG) is 3.2-0.32; or, the weight percentage of said epigallocatechin gallate (EGCG) is 23.8-75.8%, and the weight percentage of said curcumin is 24.2-76.2%, based on the total weight of said active ingredient composition for reducing body weight or body fat.

10. The composition for reducing body weight or body fat according to claim 1, wherein, the value of the ratio of the weight of said curcumin to the weight of said epigallocatechin gallate (EGCG) is 3.2-0.4; or, the weight percentage of said epigallocatechin gallate (EGCG) is 23.8-71.4%, and the weight percentage of said curcumin is 28.6-76.2%, based on the total weight of said active ingredient composition for reducing body weight or body fat.

11. The composition for reducing body weight or body fat according to claim 1, wherein said active ingredient composition for reducing body weight or body fat further comprises resveratrol.

12. A method for reducing body weight or body fat of an individual, comprising administering a therapeutically effective amount of the composition of claim 1 to an individual.

13. The method according to claim 12, wherein said composition further comprises at least one of glyceryl palmitostearate, polysorbate 20, poloxamer, and polyethylene glycols, or a combination thereof.

14. The method according to claim 12, wherein said composition further comprises piperine.

15. The method according to claim 12, wherein said polyoxyethylene stearate is polyoxyethylene (32) stearate, and the weight percentage of said polyoxyethylene (32) stearate is 0.1-20% based on the total weight of said composition; or, the weight percentage of said polysorbate 80 mixture is 0.5-20% based on the total weight of said composition; or, said polyoxyethylene stearate is polyoxyethylene (40) stearate, and the weight percentage of said polyoxyethylene (40) stearate is 0.005-6.7% based on the total weight of said composition.

16. The method according to claim 12, wherein, said polyoxyethylene stearate is polyoxyethylene (32) stearate, and the weight percentage of said polyoxyethylene (32) stearate is 1-15% based on the total weight of said composition; or, the weight percentage of said polysorbate 80 mixture is 1-15% based on the total weight of said composition; or, said polyoxyethylene stearate is polyoxyethylene (40) stearate, and the weight percentage of said polyoxyethylene (40) stearate is 0.01-3.33% based on the total weight of said composition.

17. The method according to claim 12, wherein, said polyoxyethylene stearate is polyoxyethylene (32) stearate, and the weight percentage of said polyoxyethylene (32) stearate is 1-10% based on the total weight of said composition; or, the weight percentage of said polysorbate 80 mixture is 3-10% based on the total weight of said composition; or, said polyoxyethylene stearate is polyoxyethylene (40) stearate, and the weight percentage of said polyoxyethylene (40) stearate is 0.05-1% based on the total weight of said composition.

18. The method according to claim 12, wherein, said polyoxyethylene stearate is polyoxyethylene (32) stearate, and the value of the ratio of the weight of said curcumin to the weight of said polyoxyethylene (32) stearate is 5.3-26.7; or, the value of the ratio of the weight of said curcumin to the weight of said polysorbate 80 mixture is 2-8.9; or, said polyoxyethylene stearate is polyoxyethylene (40) stearate, and the value of the ratio of the weight of said curcumin to the weight of said polyoxyethylene (40) stearate is 40-533.3; or, said polyoxyethylene stearate is polyoxyethylene (32) stearate, and the value of the ratio of the weight of said active ingredient composition for reducing body weight or body fat to the weight of said polyoxyethylene (32) stearate is 9.5-47.5; or, the value of the ratio of the weight of said active ingredient composition for reducing body weight or body fat to the weight of said polysorbate 80 mixture is 3.6-15.8; or, said polyoxyethylene stearate is polyoxyethylene (40) stearate, and the value of the ratio of the weight of said active ingredient composition for reducing body weight or body fat to the weight of said polyoxyethylene (40) stearate is 71.3-950.

19. The method according to claim 12, wherein said composition further comprises at least one of mannitol, microcrystalline celluloses, sodium dodecyl sulfate (SDS), and cross-linked sodium carboxymethyl celluloses, croscarmellose sodium or a combination thereof.

20. The method according to claim 12, wherein the value of the ratio of the weight of said curcumin to the weight of said epigallocatechin gallate (EGCG) is 3.2-0.32; or, the weight percentage of said epigallocatechin gallate (EGCG) is 23.8-75.8%, and the weight percentage of said curcumin is 24.2-76.2%, based on the total weight of said active ingredient composition for reducing body weight or body fat.

21. The method according to claim 12, wherein the value of the ratio of the weight of said curcumin to the weight of said epigallocatechin gallate (EGCG) is 3.2-0.4; or, the weight percentage of said epigallocatechin gallate (EGCG) is 23.8-71.4%, and the weight percentage of said curcumin is 28.6-76.2%, based on the total weight of said active ingredient composition for reducing body weight or body fat.

22. The method according to claim 12, wherein said active ingredient composition for reducing body weight or body fat further comprises resveratrol.

23. The method according to claim 12, wherein said composition is administered orally to said individual.

24. The method according to claim 12, wherein said individual is an individual of normal body weight, an overweight individual, an obese individual, an individual with fatty liver, or an individual with non-alcoholic steatohepatitis (NASH).

25. A method for treating fatty liver or non-alcoholic steatohepatitis, comprising administering to an individual with fatty liver or non-alcoholic steatohepatitis a therapeutically effective amount of the composition of claim 1.

26. The method according to claim 25, wherein said composition further comprises at least one of glyceryl palmitostearate, polysorbate 20, poloxamer, and polyethylene glycols, or a combination thereof.

27. The method according to claim 25, wherein said composition further comprises piperine.

28. The method according to claim 25, wherein said polyoxyethylene stearate is polyoxyethylene (32) stearate, and the weight percentage of said polyoxyethylene (32) stearate is 0.1-20% based on the total weight of said composition; or, the weight percentage of said polysorbate 80 mixture is 0.5-20% based on the total weight of said composition; or, said polyoxyethylene stearate is polyoxyethylene (40) stearate, and the weight percentage of said polyoxyethylene (40) stearate is 0.005-6.7% based on the total weight of said composition.

29. The method according to claim 25, wherein, said polyoxyethylene stearate is polyoxyethylene (32) stearate, and the value of the ratio of the weight of said curcumin to the weight of said polyoxyethylene (32) stearate is 5.3-26.7; or, the value of the ratio of the weight of said curcumin to the weight of said polysorbate 80 mixture is 2-8.9; or, said polyoxyethylene stearate is polyoxyethylene (40) stearate, and the value of the ratio of the weight of said curcumin to the weight of said polyoxyethylene (40) stearate is 40-533.3; or, said polyoxyethylene stearate is polyoxyethylene (32) stearate, and the value of the ratio of the weight of said active ingredient composition for reducing body weight or body fat to the weight of said polyoxyethylene (32) stearate is 9.5-47.5; or, the value of the ratio of the weight of said active ingredient composition for reducing body weight or body fat to the weight of said polysorbate 80 mixture is 3.6-15.8; or, said polyoxyethylene stearate is polyoxyethylene (40) stearate, and the value of the ratio of the weight of said active ingredient composition for reducing body weight or body fat to the weight of said polyoxyethylene (40) stearate is 71.3-950.

30. The method according to claim 25, wherein said composition further comprises at least one of mannitol, microcrystalline celluloses, sodium dodecyl sulfate (SDS), and cross-linked sodium carboxymethyl celluloses, or a combination thereof.

31. The method according to claim 25, wherein the value of the ratio of the weight of said curcumin to the weight of said epigallocatechin gallate (EGCG) is 3.2-0.32; or, the weight percentage of said epigallocatechin gallate (EGCG) is 23.8-75.8%, and the weight percentage of said curcumin is 24.2-76.2%, based on the total weight of said active ingredient composition for reducing body weight or body fat.

32. The method according to claim 25, wherein the value of the ratio of the weight of said curcumin to the weight of said epigallocatechin gallate (EGCG) is 3.2-0.4; or, the weight percentage of said epigallocatechin gallate (EGCG) is 23.8-71.4%, and the weight percentage of said curcumin is 28.6-76.2%, based on the total weight of said active ingredient composition for reducing body weight or body fat.

33. The method according to claim 25, wherein said composition is administered orally to said individual with fatty liver or non-alcoholic steatohepatitis.

\* \* \* \* \*